US007854731B2

(12) United States Patent
Rome et al.

(10) Patent No.: US 7,854,731 B2
(45) Date of Patent: Dec. 21, 2010

(54) VALVED CATHETER

(75) Inventors: Guy T. Rome, West Valley, UT (US);
William R. Barron, Riverton, UT (US);
Bret Hamatake, Grantsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 848 days.

(21) Appl. No.: 11/122,303

(22) Filed: May 3, 2005

(65) Prior Publication Data
US 2005/0261636 A1 Nov. 24, 2005

Related U.S. Application Data

(63) Continuation-in-part of application No. 10/803,207, filed on Mar. 18, 2004, now Pat. No. 7,094,218, and a continuation-in-part of application No. 11/076,564, filed on Mar. 8, 2005, now Pat. No. 7,578,803, which is a continuation-in-part of application No. 10/803,512, filed on Mar. 18, 2004.

(51) Int. Cl.
*A61M 1/00* (2006.01)
*A61M 25/18* (2006.01)

(52) U.S. Cl. .................. 604/540; 604/247; 604/523

(58) Field of Classification Search .................. 604/284, 604/537, 288.03, 544
See application file for complete search history.

(56) References Cited

U.S. PATENT DOCUMENTS

| 2,471,623 | A | * | 5/1949 | Hubbell ............ 137/625.18 |
| 2,709,542 | A | * | 5/1955 | Eller et al. ............ 222/209 |
| 3,176,690 | A | | 4/1965 | H'Doubler |
| D217,795 | S | | 6/1970 | Spaven |
| 3,527,226 | A | * | 9/1970 | Hakim ............ 604/9 |
| 3,565,078 | A | * | 2/1971 | Vailliancourt et al. ....... 604/256 |
| 3,572,340 | A | | 3/1971 | Lloyd et al. |
| 3,650,507 | A | | 3/1972 | Nyberg et al. |
| 3,672,372 | A | * | 6/1972 | Heimlich ............ 604/544 |
| 3,805,794 | A | | 4/1974 | Schlesigner |

(Continued)

FOREIGN PATENT DOCUMENTS

EP 1240916 A1 9/2002

(Continued)

OTHER PUBLICATIONS

Catheter, Stedman's Medical Dictionary, 2000, Lippincott Williams & Wilkins, 27th Ed.*

(Continued)

*Primary Examiner*—Tatyana Zalukaeva
*Assistant Examiner*—Paula L Craig
(74) *Attorney, Agent, or Firm*—Rutan & Tucker, LLP

(57) ABSTRACT

A valved catheter that allows placement and withdrawal of an accessing device or attachable unit without the risk of air embolism or blood loss. In one variation, the valved catheter includes a catheter tube having a necked portion in its proximal end that forms an integral valve, the necked portion being surrounded by a compression sleeve that biases the valve in a closed position. In another variation, the valved catheter is a dual lumen catheter with a corresponding bifurcating extension for engaging the valves in the catheter in order to establish fluid communication through the catheter.

7 Claims, 9 Drawing Sheets

U.S. PATENT DOCUMENTS

| | | | |
|---|---|---|---|
| 3,921,631 A | 11/1975 | Thompson | |
| 4,000,739 A | 1/1977 | Stevens | |
| 4,029,095 A | 6/1977 | Pena et al. | |
| 4,068,659 A | 1/1978 | Moorehead | |
| 4,112,949 A | 9/1978 | Rosenthal et al. | |
| 4,123,091 A | 10/1978 | Cosentino et al. | |
| 4,134,402 A | 1/1979 | Mahurkar | |
| 4,198,973 A | 4/1980 | Millet | |
| 4,233,974 A | 11/1980 | Desecki et al. | |
| 4,235,232 A * | 11/1980 | Spaven et al. | 604/178 |
| 4,256,106 A | 3/1981 | Shoor | |
| 4,256,116 A | 3/1981 | Meretsky et al. | |
| 4,267,835 A | 5/1981 | Barger et al. | |
| 4,296,747 A | 10/1981 | Ogle | |
| 4,306,562 A | 12/1981 | Osborne | |
| 4,340,052 A | 7/1982 | Dennehey et al. | |
| 4,387,879 A * | 6/1983 | Tauschinski | 251/149.1 |
| 4,391,029 A | 7/1983 | Czuba et al. | |
| 4,411,654 A | 10/1983 | Boarini et al. | |
| 4,412,832 A | 11/1983 | Kling et al. | |
| 4,424,833 A | 1/1984 | Spector et al. | |
| D272,651 S | 2/1984 | Mahurkar | |
| 4,430,081 A | 2/1984 | Timmermans | |
| 4,431,426 A | 2/1984 | Groshong et al. | |
| 4,432,759 A | 2/1984 | Gross et al. | |
| 4,436,519 A | 3/1984 | O'Neill | |
| 4,439,179 A * | 3/1984 | Lueders et al. | 604/34 |
| 4,445,893 A | 5/1984 | Bodicky | |
| 4,449,973 A | 5/1984 | Luther | |
| 4,468,224 A | 8/1984 | Enzmann et al. | |
| 4,473,067 A | 9/1984 | Schiff | |
| 4,490,003 A | 12/1984 | Robinson | |
| RE31,855 E | 3/1985 | Osborne | |
| 4,512,766 A * | 4/1985 | Vailancourt | 604/167.03 |
| 4,539,003 A | 9/1985 | Tucker | |
| 4,543,087 A | 9/1985 | Sommercorn et al. | |
| 4,553,959 A * | 11/1985 | Hickey et al. | 604/103.09 |
| 4,557,261 A | 12/1985 | Riigheimer | |
| 4,568,329 A | 2/1986 | Mahurkar | |
| 4,571,241 A | 2/1986 | Christopher | |
| 4,573,974 A | 3/1986 | Ruschke | |
| 4,581,012 A | 4/1986 | Brown et al. | |
| 4,581,025 A | 4/1986 | Timmermans | |
| 4,583,968 A | 4/1986 | Mahurkar | |
| 4,591,355 A | 5/1986 | Hilse | |
| 4,592,749 A | 6/1986 | Ebling et al. | |
| 4,596,559 A | 6/1986 | Fleischhacker | |
| 4,596,571 A | 6/1986 | Bellotti et al. | |
| 4,610,665 A | 9/1986 | Matsumoto et al. | |
| 4,619,643 A | 10/1986 | Bai | |
| 4,623,327 A | 11/1986 | Mahurkar | |
| 4,626,245 A | 12/1986 | Weinstein | |
| 4,643,711 A | 2/1987 | Bates | |
| 4,650,472 A | 3/1987 | Bates | |
| 4,673,393 A | 6/1987 | Suzuki et al. | |
| 4,675,004 A | 6/1987 | Hadford et al. | |
| 4,675,020 A | 6/1987 | McPhee | |
| 4,681,122 A | 7/1987 | Winters et al. | |
| 4,682,978 A | 7/1987 | Martin | |
| 4,692,141 A | 9/1987 | Mahurkar | |
| 4,701,159 A | 10/1987 | Brown et al. | |
| 4,722,725 A | 2/1988 | Sawyer et al. | |
| 4,723,550 A | 2/1988 | Bales et al. | |
| 4,723,948 A | 2/1988 | Clark et al. | |
| 4,726,374 A | 2/1988 | Bales et al. | |
| 4,738,658 A | 4/1988 | Magro et al. | |
| 4,743,265 A | 5/1988 | Whitehouse et al. | |
| 4,747,833 A | 5/1988 | Kousai et al. | |
| 4,753,765 A | 6/1988 | Pande | |
| 4,770,652 A | 9/1988 | Mahurkar | |
| 4,772,266 A | 9/1988 | Groshong | |
| 4,772,268 A | 9/1988 | Bates | |
| 4,776,841 A | 10/1988 | Catalano | |
| 4,784,644 A | 11/1988 | Sawyer et al. | |
| 4,795,426 A | 1/1989 | Jones | |
| 4,798,594 A | 1/1989 | Hillstead | |
| 4,808,155 A | 2/1989 | Mahurkar | |
| 4,842,582 A | 6/1989 | Mahurkar | |
| 4,842,592 A | 6/1989 | Caggiani et al. | |
| 4,850,955 A | 7/1989 | Newkirk | |
| 4,865,593 A | 9/1989 | Ogawa et al. | |
| 4,874,377 A | 10/1989 | Newgard et al. | |
| 4,895,561 A | 1/1990 | Mahurkar | |
| 4,909,798 A | 3/1990 | Fleischhacker et al. | |
| RE33,219 E * | 5/1990 | Daniell et al. | 251/7 |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,932,938 A * | 6/1990 | Goldberg et al. | 604/99.04 |
| 4,935,010 A | 6/1990 | Cox et al. | |
| 4,936,826 A | 6/1990 | Amarasinghe | |
| 4,946,133 A | 8/1990 | Johnson et al. | |
| 4,946,449 A * | 8/1990 | Davis, Jr. | 604/256 |
| 4,952,359 A | 8/1990 | Wells | |
| 4,960,412 A | 10/1990 | Fink | |
| 4,966,588 A | 10/1990 | Rayman et al. | |
| 4,983,168 A | 1/1991 | Moorehead | |
| 4,997,424 A | 3/1991 | Little | |
| 5,007,901 A | 4/1991 | Shields | |
| 5,035,686 A | 7/1991 | Crittenden et al. | |
| 5,041,095 A | 8/1991 | Littrell | |
| 5,053,003 A * | 10/1991 | Dadson et al. | 604/28 |
| 5,053,004 A | 10/1991 | Markel et al. | |
| 5,053,013 A * | 10/1991 | Ensminger et al. | 604/167.04 |
| 5,053,014 A | 10/1991 | Van Heugten | |
| 5,053,023 A | 10/1991 | Martin | |
| 5,057,073 A | 10/1991 | Martin | |
| 5,059,170 A * | 10/1991 | Cameron | 604/43 |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,106,368 A * | 4/1992 | Uldall et al. | 604/43 |
| 5,108,380 A | 4/1992 | Herlitze et al. | |
| 5,112,301 A | 5/1992 | Fenton, Jr. et al. | |
| 5,112,323 A | 5/1992 | Winkler et al. | |
| 5,114,408 A | 5/1992 | Fleischhaker et al. | |
| 5,117,836 A | 6/1992 | Millar | |
| 5,125,904 A | 6/1992 | Lee | |
| 5,135,599 A | 8/1992 | Martin et al. | |
| 5,137,524 A | 8/1992 | Lynn et al. | |
| 5,141,497 A | 8/1992 | Erskine | |
| 5,149,327 A | 9/1992 | Oshiyama | |
| 5,154,701 A | 10/1992 | Cheer et al. | |
| 5,156,592 A | 10/1992 | Martin et al. | |
| 5,156,596 A * | 10/1992 | Balbierz et al. | 604/164.11 |
| 5,158,545 A * | 10/1992 | Trudell et al. | 604/509 |
| 5,158,553 A * | 10/1992 | Berry et al. | 604/248 |
| 5,160,323 A | 11/1992 | Andrew | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,180,372 A | 1/1993 | Vegoe et al. | |
| 5,186,431 A * | 2/1993 | Tamari | 251/5 |
| 5,188,593 A | 2/1993 | Martin | |
| 5,190,520 A | 3/1993 | Fenton, Jr. et al. | |
| 5,190,528 A | 3/1993 | Fonger et al. | |

| Patent | Date | Inventor |
|---|---|---|
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,976 A | 3/1993 | Herweck et al. |
| 5,201,722 A | 4/1993 | Moorehead et al. |
| 5,205,834 A | 4/1993 | Moorehead et al. |
| 5,207,650 A | 5/1993 | Martin |
| 5,209,723 A | 5/1993 | Twardowski et al. |
| 5,211,633 A | 5/1993 | Stouder, Jr. |
| 5,215,538 A | 6/1993 | Larkin |
| 5,221,255 A | 6/1993 | Mahurkar et al. |
| 5,221,256 A | 6/1993 | Mahurkar |
| 5,221,263 A | 6/1993 | Sinko et al. |
| 5,234,410 A | 8/1993 | Graham et al. |
| 5,242,413 A | 9/1993 | Heiliger |
| 5,242,430 A | 9/1993 | Arenas et al. |
| 5,250,033 A | 10/1993 | Evans et al. |
| 5,251,873 A | 10/1993 | Atkinson et al. |
| 5,255,691 A | 10/1993 | Otten |
| 5,273,540 A | 12/1993 | Luther et al. |
| 5,273,546 A | 12/1993 | McLaughlin et al. |
| 5,275,583 A | 1/1994 | Crainich |
| 5,279,597 A * | 1/1994 | Dassa et al. .................. 604/535 |
| 5,290,294 A | 3/1994 | Cox et al. |
| 5,304,142 A | 4/1994 | Liebl et al. |
| 5,304,156 A | 4/1994 | Sylvanowicz et al. |
| 5,312,337 A | 5/1994 | Flaherty et al. |
| 5,312,355 A | 5/1994 | Lee |
| 5,312,357 A | 5/1994 | Buijs et al. |
| 5,320,602 A | 6/1994 | Karpiel |
| 5,324,271 A | 6/1994 | Abiuso et al. |
| 5,324,274 A | 6/1994 | Martin |
| 5,330,437 A * | 7/1994 | Durman .................. 604/167.04 |
| 5,334,157 A | 8/1994 | Klein et al. |
| 5,334,187 A | 8/1994 | Fischell et al. |
| 5,336,192 A | 8/1994 | Palestrant |
| 5,338,313 A * | 8/1994 | Mollenauer et al. ......... 604/249 |
| 5,342,386 A | 8/1994 | Trotta |
| 5,348,537 A | 9/1994 | Wiesner et al. |
| 5,350,358 A | 9/1994 | Martin |
| 5,350,362 A | 9/1994 | Stouder, Jr. |
| 5,350,363 A | 9/1994 | Goode et al. |
| 5,360,397 A | 11/1994 | Pinchuk |
| 5,360,403 A * | 11/1994 | Mische .................. 604/101.02 |
| 5,364,393 A | 11/1994 | Auth et al. |
| 5,368,574 A | 11/1994 | Antonacci et al. |
| 5,374,245 A | 12/1994 | Mahurkar |
| 5,378,230 A | 1/1995 | Mahurkar |
| 5,380,276 A | 1/1995 | Miller et al. |
| 5,382,241 A | 1/1995 | Choudhury et al. |
| 5,389,090 A | 2/1995 | Fischell et al. |
| 5,391,152 A | 2/1995 | Patterson |
| 5,395,352 A | 3/1995 | Penny |
| 5,397,311 A | 3/1995 | Walker et al. |
| 5,399,172 A | 3/1995 | Martin et al. |
| 5,401,245 A | 3/1995 | Haining |
| 5,405,320 A | 4/1995 | Twardowski et al. |
| 5,405,323 A | 4/1995 | Rogers et al. |
| 5,405,341 A | 4/1995 | Martin |
| 5,407,434 A * | 4/1995 | Gross .................... 604/167.02 |
| 5,409,463 A | 4/1995 | Thomas et al. |
| 5,409,464 A | 4/1995 | Villalobos |
| 5,409,469 A | 4/1995 | Schaerf |
| 5,409,644 A | 4/1995 | Martin et al. |
| 5,413,561 A | 5/1995 | Fischell et al. |
| 5,415,320 A | 5/1995 | North et al. |
| 5,417,668 A | 5/1995 | Setzer et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,445,613 A * | 8/1995 | Orth ........................... 604/66 |
| 5,453,095 A | 9/1995 | Davila et al. |
| 5,454,409 A | 10/1995 | McAffer et al. |
| 5,460,616 A | 10/1995 | Weinstein et al. |
| 5,472,417 A | 12/1995 | Martin et al. |
| 5,472,418 A | 12/1995 | Palestrant |
| 5,472,432 A * | 12/1995 | Martin ....................... 604/248 |
| 5,472,435 A | 12/1995 | Sutton |
| 5,474,099 A | 12/1995 | Boehmer et al. |
| 5,474,540 A | 12/1995 | Miller et al. |
| 5,480,380 A | 1/1996 | Martin |
| 5,484,401 A | 1/1996 | Rodriguez |
| 5,486,159 A | 1/1996 | Mahurkar |
| 5,488,960 A | 2/1996 | Toner |
| 5,496,299 A | 3/1996 | Felix et al. |
| 5,496,346 A | 3/1996 | Horzewski et al. |
| 5,501,676 A | 3/1996 | Niedospial et al. |
| 5,507,733 A | 4/1996 | Larkin et al. |
| 5,509,897 A | 4/1996 | Twardowski et al. |
| 5,514,117 A | 5/1996 | Lynn |
| 5,520,655 A | 5/1996 | Davila et al. |
| 5,520,665 A | 5/1996 | Fleetwood et al. |
| 5,522,806 A * | 6/1996 | Schonbachler et al. ....... 604/250 |
| 5,536,255 A | 7/1996 | Moss |
| 5,538,505 A | 7/1996 | Weinstein et al. |
| 5,542,931 A | 8/1996 | Gravener et al. |
| 5,556,387 A | 9/1996 | Mollenauer et al. |
| 5,569,182 A | 10/1996 | Twardowski et al. |
| 5,599,305 A | 2/1997 | Hermann et al. |
| 5,613,953 A | 3/1997 | Patterson et al. |
| 5,613,956 A | 3/1997 | Pohndorf |
| 5,624,413 A | 4/1997 | Markel et al. |
| 5,632,729 A * | 5/1997 | Cai et al. ................ 604/288.01 |
| 5,636,875 A | 6/1997 | Wasser et al. |
| 5,637,102 A | 6/1997 | Tolkoff et al. |
| 5,647,857 A | 7/1997 | Anderson et al. |
| 5,651,776 A | 7/1997 | Appling et al. |
| 5,653,698 A | 8/1997 | Niedospial et al. |
| 5,672,158 A | 9/1997 | Okada et al. |
| 5,685,856 A | 11/1997 | Lehrer |
| 5,685,867 A | 11/1997 | Twardowski et al. |
| 5,702,370 A | 12/1997 | Sylvanowicz et al. |
| 5,702,374 A | 12/1997 | Johnson |
| 5,704,915 A | 1/1998 | Melsky et al. |
| 5,713,867 A | 2/1998 | Morris |
| 5,718,678 A | 2/1998 | Fleming, III |
| 5,718,692 A | 2/1998 | Schon et al. |
| 5,725,506 A | 3/1998 | Freeman et al. |
| 5,735,819 A | 4/1998 | Elliott |
| 5,741,233 A | 4/1998 | Riddle et al. |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,628 A * | 6/1998 | Bacich et al. .................. 604/43 |
| 5,772,643 A | 6/1998 | Howell et al. |
| 5,772,678 A | 6/1998 | Thomason et al. |
| 5,776,111 A | 7/1998 | Tesio |
| 5,782,505 A | 7/1998 | Brooks et al. |
| 5,782,807 A | 7/1998 | Falvai et al. |
| 5,782,817 A | 7/1998 | Franzel et al. |
| 5,785,694 A * | 7/1998 | Cohen et al. ................. 604/250 |
| 5,797,869 A | 8/1998 | Martin et al. |
| 5,800,414 A | 9/1998 | Cazal |
| 5,807,311 A * | 9/1998 | Palestrant ..................... 604/28 |
| 5,810,789 A | 9/1998 | Powers et al. |
| 5,843,031 A | 12/1998 | Hermann et al. |
| 5,843,046 A * | 12/1998 | Motisi et al. ................. 604/256 |
| 5,853,393 A | 12/1998 | Bogert |
| 5,858,007 A | 1/1999 | Fagan et al. |
| 5,865,721 A | 2/1999 | Andrews et al. |
| 5,879,333 A | 3/1999 | Smith |
| 5,885,217 A | 3/1999 | Gisselberg et al. |

| Patent No. | Date | Inventor | Ref |
|---|---|---|---|
| 5,895,376 A * | 4/1999 | Schwartz et al. | 604/256 |
| 5,897,533 A * | 4/1999 | Glickman | 604/256 |
| 5,911,710 A | 6/1999 | Barry et al. | |
| 5,916,194 A | 6/1999 | Jacobsen et al. | |
| 5,919,160 A | 7/1999 | Sanfilippo, II | |
| 5,921,968 A | 7/1999 | Lampropoulos et al. | |
| 5,935,112 A | 8/1999 | Stevens et al. | |
| 5,944,695 A | 8/1999 | Johnson et al. | |
| 5,944,732 A | 8/1999 | Raulerson et al. | |
| 5,947,953 A | 9/1999 | Ash et al. | |
| 5,951,518 A | 9/1999 | Licata et al. | |
| 5,957,912 A | 9/1999 | Heitzmann | |
| 5,961,485 A | 10/1999 | Martin | |
| 5,961,486 A | 10/1999 | Twardowski et al. | |
| 5,967,490 A | 10/1999 | Pike | |
| 5,971,958 A | 10/1999 | Zhang | |
| 5,976,103 A | 11/1999 | Martin | |
| 5,989,213 A | 11/1999 | Maginot | |
| 5,997,486 A | 12/1999 | Burek et al. | |
| 6,024,729 A | 2/2000 | Dehdashtian et al. | |
| 6,027,480 A | 2/2000 | Davis et al. | |
| 6,033,375 A | 3/2000 | Brumbach | |
| 6,033,388 A | 3/2000 | Nordstrom et al. | |
| 6,036,171 A | 3/2000 | Weinheimer et al. | |
| 6,053,904 A | 4/2000 | Scribner et al. | |
| 6,068,011 A | 5/2000 | Paradis | |
| 6,074,374 A | 6/2000 | Fulton | |
| 6,074,377 A | 6/2000 | Sanfilippo, II | |
| 6,074,379 A | 6/2000 | Prichard | |
| 6,083,207 A | 7/2000 | Heck | |
| 6,086,555 A | 7/2000 | Eliasen et al. | |
| 6,086,570 A | 7/2000 | Aboul-Hosn et al. | |
| 6,088,889 A | 7/2000 | Luther et al. | |
| 6,090,083 A | 7/2000 | Sell et al. | |
| 6,093,154 A | 7/2000 | Burek et al. | |
| 6,096,011 A | 8/2000 | Trombley, III et al. | |
| 6,099,519 A | 8/2000 | Olsen et al. | |
| 6,106,503 A | 8/2000 | Pfeiderer et al. | |
| 6,106,540 A | 8/2000 | White et al. | |
| 6,120,476 A | 9/2000 | Fung et al. | |
| 6,120,480 A | 9/2000 | Zhang et al. | |
| 6,132,407 A | 10/2000 | Genese et al. | |
| 6,142,981 A | 11/2000 | Heck et al. | |
| 6,155,610 A | 12/2000 | Godeau et al. | |
| 6,156,016 A | 12/2000 | Maginot | |
| 6,159,198 A | 12/2000 | Gardeski et al. | |
| 6,162,196 A | 12/2000 | Hart et al. | |
| 6,171,281 B1 | 1/2001 | Zhang | |
| 6,179,806 B1 * | 1/2001 | Sansoucy | 604/30 |
| 6,190,349 B1 | 2/2001 | Ash et al. | |
| 6,190,352 B1 | 2/2001 | Haarala et al. | |
| 6,190,371 B1 | 2/2001 | Maginot et al. | |
| 6,206,849 B1 | 3/2001 | Martin et al. | |
| 6,210,366 B1 | 4/2001 | Sanfilippo, II | |
| 6,213,988 B1 | 4/2001 | McIvor et al. | |
| 6,221,057 B1 | 4/2001 | Schwartz et al. | |
| 6,228,060 B1 * | 5/2001 | Howell | 604/167.04 |
| 6,228,062 B1 | 5/2001 | Howell et al. | |
| 6,258,058 B1 | 7/2001 | Sanfilippo, II | |
| 6,273,871 B1 | 8/2001 | Davis et al. | |
| 6,276,661 B1 | 8/2001 | Laird | |
| 6,293,927 B1 | 9/2001 | McGuckin, Jr. | |
| 6,322,541 B2 | 11/2001 | West et al. | |
| 6,331,176 B1 | 12/2001 | Becker et al. | |
| 6,332,874 B1 | 12/2001 | Eliasen et al. | |
| 6,338,725 B1 | 1/2002 | Hermann et al. | |
| 6,344,033 B1 | 2/2002 | Jepson et al. | |
| 6,352,520 B1 | 3/2002 | Miyazaki | |
| 6,402,723 B1 | 6/2002 | Lampropoulos et al. | |
| 6,413,250 B1 | 7/2002 | Smith | |
| 6,423,050 B1 | 7/2002 | Twardowski | |
| 6,423,053 B1 | 7/2002 | Lee | |
| 6,454,744 B1 | 9/2002 | Spohn et al. | |
| 6,458,103 B1 | 10/2002 | Albert et al. | |
| 6,494,860 B2 | 12/2002 | Rocamora et al. | |
| 6,497,681 B1 | 12/2002 | Brenner | |
| 6,508,790 B1 | 1/2003 | Lawrence | |
| 6,508,807 B1 | 1/2003 | Peters | |
| 6,520,939 B2 | 2/2003 | Lafontaine | |
| 6,544,247 B1 | 4/2003 | Gardeski et al. | |
| 6,551,283 B1 | 4/2003 | Guo et al. | |
| 6,562,023 B1 * | 5/2003 | Marrs et al. | 604/533 |
| 6,575,960 B2 | 6/2003 | Becker et al. | |
| 6,589,262 B1 | 7/2003 | Honebrink et al. | |
| 6,592,544 B1 | 7/2003 | Mooney et al. | |
| 6,592,558 B2 * | 7/2003 | Quah | 604/250 |
| 6,592,565 B2 | 7/2003 | Twardowski | |
| 6,623,460 B1 | 9/2003 | Heck | |
| 6,626,418 B2 | 9/2003 | Kiehne et al. | |
| 6,629,350 B2 * | 10/2003 | Motsenbocker | 29/283.5 |
| 6,632,200 B2 | 10/2003 | Guo et al. | |
| 6,638,242 B2 | 10/2003 | Wilson et al. | |
| 6,641,574 B2 * | 11/2003 | Badia Segura | 604/533 |
| 6,645,178 B1 | 11/2003 | Junker et al. | |
| 6,663,595 B2 | 12/2003 | Spohn et al. | |
| 6,669,681 B2 | 12/2003 | Jepson et al. | |
| 6,682,498 B2 | 1/2004 | Ross | |
| 6,682,519 B1 | 1/2004 | Schon | |
| 6,689,109 B2 * | 2/2004 | Lynn | 604/250 |
| 6,692,464 B2 | 2/2004 | Graf | |
| 6,695,832 B2 | 2/2004 | Schon et al. | |
| 6,712,796 B2 * | 3/2004 | Fentis et al. | 604/247 |
| 6,719,749 B1 | 4/2004 | Schweikert et al. | |
| 6,722,705 B2 | 4/2004 | Korkor | |
| 6,827,710 B1 | 12/2004 | Mooney et al. | |
| 6,843,513 B2 | 1/2005 | Guala | |
| 6,872,198 B1 | 3/2005 | Wilson et al. | |
| 6,881,211 B2 | 4/2005 | Schweikert et al. | |
| D505,202 S | 5/2005 | Chesnin | |
| 6,887,220 B2 * | 5/2005 | Hogendijk | 604/119 |
| 6,893,056 B2 | 5/2005 | Guala | |
| 6,916,051 B2 | 7/2005 | Fisher | |
| 6,916,313 B2 | 7/2005 | Cunningham | |
| 6,921,396 B1 | 7/2005 | Wilson et al. | |
| 6,932,795 B2 * | 8/2005 | Lopez et al. | 604/249 |
| 6,969,381 B2 | 11/2005 | Voorhees | |
| 6,971,390 B1 | 12/2005 | Vasek et al. | |
| 7,044,441 B2 | 5/2006 | Doyle | |
| 7,048,724 B2 | 5/2006 | Grossman et al. | |
| 7,094,218 B2 * | 8/2006 | Rome et al. | 604/99.04 |
| 7,163,531 B2 * | 1/2007 | Seese et al. | 604/533 |
| 7,182,746 B2 | 2/2007 | Haarala et al. | |
| 7,258,685 B2 | 8/2007 | Kerr | |
| 7,300,430 B2 | 11/2007 | Wilson et al. | |
| 7,347,853 B2 * | 3/2008 | DiFiore et al. | 604/537 |
| 7,377,915 B2 | 5/2008 | Rasmussen et al. | |
| 7,470,261 B2 * | 12/2008 | Lynn | 604/256 |
| 7,578,803 B2 | 8/2009 | Rome et al. | |
| 7,594,910 B2 | 9/2009 | Butts et al. | |
| 7,594,911 B2 | 9/2009 | Powers et al. | |
| 2001/0041857 | 11/2001 | Sansoucy | |
| 2001/0041873 A1 | 11/2001 | Dopper et al. | |
| 2002/0010437 A1 | 1/2002 | Lopez et al. | |
| 2002/0077605 A1 * | 6/2002 | Fentis et al. | 604/247 |
| 2002/0099326 A1 | 7/2002 | Wilson et al. | |
| 2002/0099327 A1 | 7/2002 | Wilson et al. | |
| 2002/0128604 A1 | 9/2002 | Nakajima | |
| 2002/0147431 A1 * | 10/2002 | Lopez et al. | 604/256 |
| 2003/0065288 A1 | 4/2003 | Brimhall et al. | |
| 2003/0066218 A1 | 4/2003 | Schweikert | |
| 2003/0088213 A1 * | 5/2003 | Schweikert et al. | 604/177 |
| 2003/0153898 A1 | 8/2003 | Schon et al. | |
| 2003/0187411 A1 | 10/2003 | Constantz | |
| 2003/0199853 A1 | 10/2003 | Olsen et al. | |
| 2003/0201639 A1 | 10/2003 | Korkor | |
| 2003/0225379 A1 * | 12/2003 | Schaffer et al. | 604/250 |

| | | | |
|---|---|---|---|
| 2004/0065333 | A1 | 4/2004 | Wilson et al. |
| 2004/0082923 | A1 | 4/2004 | Field |
| 2004/0092863 | A1 | 5/2004 | Raulerson et al. |
| 2004/0097903 | A1 | 5/2004 | Raulerson |
| 2004/0122418 | A1 | 6/2004 | Voorhees |
| 2004/0158208 | A1 | 8/2004 | Hiejima |
| 2004/0167463 | A1 | 8/2004 | Zawacki et al. |
| 2004/0167478 | A1 | 8/2004 | Mooney et al. |
| 2004/0171997 | A1 | 9/2004 | Wilson et al. |
| 2004/0172003 | A1 | 9/2004 | Wilson et al. |
| 2004/0176739 | A1 | 9/2004 | Stephens et al. |
| 2004/0183305 | A1 | 9/2004 | Fisher |
| 2004/0186444 | A1 | 9/2004 | Daly et al. |
| 2004/0186445 | A1 | 9/2004 | Raulerson et al. |
| 2004/0193119 | A1 | 9/2004 | Canaud et al. |
| 2004/0243095 | A1 | 12/2004 | Nimkar et al. |
| 2005/0049555 | A1 | 3/2005 | Moorehead et al. |
| 2005/0080398 | A1 | 4/2005 | Markel et al. |
| 2005/0085765 | A1 | 4/2005 | Voorhees |
| 2005/0085794 | A1 | 4/2005 | Denoth et al. |
| 2005/0095891 | A1 | 5/2005 | Schorn |
| 2005/0096585 | A1 | 5/2005 | Schon et al. |
| 2005/0113805 | A1 | 5/2005 | Devellian et al. |
| 2005/0187535 | A1 | 8/2005 | Wilson et al. |
| 2005/0209572 | A1 | 9/2005 | Rome et al. |
| 2005/0209581 | A1* | 9/2005 | Butts et al. .................. 604/523 |
| 2005/0209584 | A1* | 9/2005 | Rome .......................... 604/536 |
| 2005/0256461 | A1* | 11/2005 | DiFiore et al. ............... 604/247 |
| 2005/0261664 | A1* | 11/2005 | Rome et al. .................. 604/508 |
| 2005/0261665 | A1 | 11/2005 | Voorhees |
| 2006/0015074 | A1* | 1/2006 | Lynn .......................... 604/250 |
| 2006/0015086 | A1* | 1/2006 | Rasmussen et al. ......... 604/533 |
| 2006/0084929 | A1 | 4/2006 | Eliasen |
| 2006/0129134 | A1 | 6/2006 | Kerr |
| 2006/0276773 | A1 | 12/2006 | Wilson et al. |
| 2007/0016167 | A1 | 1/2007 | Smith et al. |
| 2007/0060866 | A1 | 3/2007 | Raulerson et al. |
| 2008/0009832 | A1 | 1/2008 | Barron et al. |
| 2008/0200901 | A1 | 8/2008 | Rasmussen et al. |
| 2009/0013944 | A1 | 1/2009 | Re Fiorentin et al. |
| 2009/0137944 | A1 | 5/2009 | Haarala et al. |
| 2010/0010445 | A1 | 1/2010 | Powers et al. |
| 2010/0016838 | A1 | 1/2010 | Butts et al. |

FOREIGN PATENT DOCUMENTS

| | | |
|---|---|---|
| WO | WO 97/22374 | 6/1997 |
| WO | WO-9722374 A1 | 6/1997 |
| WO | WO 00/23137 | 4/2000 |
| WO | WO-0023137 | 4/2000 |

OTHER PUBLICATIONS

Catheter, 2003, Webster's New World Medical Dictionary, Credo Reference.*
Camp, L. Dawn, "Care of the Groshong Catheter", Oncol. Nurs. Forum, pp. 745-749, vol. 15, No. 6, 1988.*
Health Devices May-Jun. 1998; 25(5-6):214-5.
Camp, "Care of the Groshong Catheter", Oncol Nurs Forum, vol. 15, No. 6, 1988.
Delmore et al., "Experience with the Groshong Long-Term Central Venous Catheter", Gynecologic Oncology 34, 216-218 (1989).
Malviya et al., "Vascular Access in Gynecological Cancer Using the Groshong Right Atrial Catheter", Gynecological Oncology 33, 313-316 (1989).
Mar. 9, 2006 Non-Final Office Action for U.S. Appl. No. 11/076,564, filed Mar. 8, 2005.
Aug. 25, 2006 Final Office Action for U.S. Appl. No. 11/076,564, filed Mar. 8, 2005.
Feb. 9, 2007 Non-Final Office Action for U.S. Appl. No. 11/076,564, filed Mar. 8, 2005.
Jul. 27, 2007 Final Office Action for U.S. Appl. No. 11/076,564, filed Mar. 8, 2005.
Jul. 22, 2009 Non-Final Office Action for U.S. Appl. No. 10/803,512, filed Mar. 18, 2004.
May 30, 2008 Final Office Action for U.S. Appl. No. 10/803,512, filed Mar. 18, 2004.
Jan. 24, 2008 Non-Final Office Action for U.S. Appl. No. 10/803,512, filed Mar. 18, 2004.
Jan. 23, 2008 Non-Final Office Action for U.S. Appl. No. 11/076,564, filed Mar. 8, 2005.
Dec. 17, 2008 Non-Final Office Action for U.S. Appl. No. 11/076,564, filed Mar. 8, 2005.
Sep. 19, 2005 Non-Final Office Action for U.S. Appl. No. 10/803,207, filed Mar. 18, 2004.
U.S. Appl. No. 10/803,207 filed Mar. 18, 2004 Notice of Allowance dated Apr. 21, 2006.
U.S. Appl. No. 10/803,279 filed Mar. 18, 2004, Advisory Action dated Aug. 22, 2007.
U.S. Appl. No. 10/803,279 filed Mar. 18, 2004, Final Office Action dated May 31, 2007.
U.S. Appl. No. 10/803,279 filed Mar. 18, 2004, Final Office Action dated Oct. 1, 2008.
U.S. Appl. No. 10/803,279 filed Mar. 18, 2004, Non-Final Office Action dated Apr. 2, 2009.
U.S. Appl. No. 10/803,279 filed Mar. 18, 2004, Non-Final Office Action dated Dec. 1, 2006.
U.S. Appl. No. 10/803,279 filed Mar. 18, 2004, Non-Final Office Action dated Jun. 5, 2006.
U.S. Appl. No. 10/803,279 filed Mar. 18, 2004, Non-Final Office Action dated Sep. 20, 2007.
U.S. Appl. No. 10/803,279 filed Mar. 18, 2004, Notice of Allowance dated May 28, 2009.
U.S. Appl. No. 10/803,512 filed Mar. 18, 2004 Advisory Action dated Oct. 16, 2008.
U.S. Appl. No. 10/803,512 filed Mar. 18, 2004 Non-Final Office Action dated May 24, 2010.
U.S. Appl. No. 10/803,513 filed Mar. 18, 2004 Non-Final Office Action Jul. 25, 2008.
U.S. Appl. No. 10/803,513 filed Mar. 18, 2004 Notice of Allowance dated Jun. 12, 2009.
U.S. Appl. No. 11/076,564 filed Mar. 8, 2005 Advisory Action Nov. 16, 2006.
U.S. Appl. No. 11/076,564 filed Mar. 8, 2005 Notice of Allowance dated Jun. 17, 2009.
U.S. Appl. No. 11/096,553 filed Apr. 1, 2005 Advisory Action dated Aug. 1, 2007.
U.S. Appl. No. 11/096,553 filed Apr. 1, 2005 Final Office Action dated Feb. 27, 2007.
U.S. Appl. No. 11/096,553 filed Apr. 1, 2005 Non-Final Office Action dated Jan. 24, 2006.
U.S. Appl. No. 11/096,553 filed Apr. 1, 2005 Non-Final Office Action dated May 19, 2006.
U.S. Appl. No. 11/096,553 filed Apr. 1, 2005 Non-Final Office Action dated Oct. 10, 2007.
U.S. Appl. No. 11/096,553 filed Apr. 1, 2005 Notice of Allowance dated Mar. 25, 2008.
U.S. Appl. No. 11/471,193 filed Jun. 20, 2006, Non-Final Office Action dated Jan. 14, 2010.
U.S. Appl. No. 11/471,193 filed Jun. 20, 2006, Notice of Allowance dated Jul. 26, 2010.
U.S. Appl. No. 12/106,704 filed Apr. 21, 2008 Final Office Action dated Apr. 15, 2010.
U.S. Appl. No. 12/106,704 filed Apr. 21, 2008 Non-Final Office Action dated Apr. 27, 2009.
U.S. Appl. No. 12/106,704 filed Apr. 21, 2008 Non-Final Office Action dated Oct. 22, 2009.
U.S. Appl. No. 12/563,776 filed Sep. 21, 2009 Non-Final Office Action dated Jun. 16, 2010.

* cited by examiner

VALVED CATHETER

CROSS-REFERENCE TO RELATED APPLICATIONS

This application is a continuation-in-part of U.S. patent application Ser. No. 10/803,207, entitled "VALVED CATHETER," filed Mar. 18, 2004, now U.S. Pat. No. 7,094,218, and also a continuation-in-part of U.S. patent application Ser. No. 11/076,564, entitled "MULTIFUNCTION ADAPTOR FOR AN OPEN-ENDED CATHETER," filed Mar. 8, 2005, now U.S. Pat. No. 7,578,803, which is a continuation-in-part of U.S. patent application Ser. No. 10/803,512, entitled "MULTIFUNCTION ADAPTOR FOR AN OPEN-ENDED CATHETER," filed Mar. 18, 2004, each of which is incorporated herein by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

There are a variety of conditions that require injection of fluids into, or withdrawing fluids from, parts of a body below the surface of the skin of the body. During the procedure, symptomatic gas embolism can occur when undissolved gas (e.g., air, $CO_2$, etc.) accumulates in the heart and/or pulmonary arteries. This gas can compromise the circulation of blood through the lungs, causing serious injury or death. *Health Devices* May-June 1996; 25(5-6):214-5 reported a case of suspected gas embolism. During a hysteroscopy (performed with a patient under intravenous sedation), the patient gasped for air almost immediately upon uterine insufflation. Based on the clinical signs, the medical staff suspected that the patient's condition was caused by a $CO_2$ embolism that originated in the uterus. However, a follow up investigation revealed that the embolized gas was probably air, not $CO_2$. The air may have been introduced into the patient from the dead space in the tubing set used to connect the insufflator to the hysteroscope. This tubing set was not purged before insufflation began. *Health Devices* recommended that before delivering a fluid to a patient, one must purge air from tubing sets and instruments. Thus, there is a need for a valved catheter wherein the valved catheter comprises a safety valve having minimal dead space built-in the catheter tube that would automatically close to reduce the risk of blood loss or air embolism if an attachment to the catheter were to be inadvertently disconnected from the catheter tube.

A subcutaneously tunneled catheter is often selected when a catheter might be required to be implanted within a patient for weeks to months. A subcutaneously tunneled catheter can be implanted or removed in the outpatient setting and has a decreased incidence of infection. The typical procedure for implanting the tunneled catheter is by forward tunneling. However, another method of implanting the tunneled catheter is by reverse tunneling, as follows: (a) place the distal end of a catheter within a blood vessel through an entry site; (b) mark an exit location of a tunnel to be formed in a subcutaneous plane; (c) create a subcutaneous channel from the exit to entry site using a tunneler by pushing the tapered end of the tunneler through the skin; (d) attach the proximal end of the catheter to the tapered end of the tunneler; (e) pull the tunneler with the secured catheter from the entry to the exit site, through the subcutaneous channel, while gently holding the catheter distal to the cuff; and (f) detach the catheter from the tunneler and attach a bifurcation element thereto. During the described reverse tunneling technique, the proximal end of a typical catheter tube is open, permitting the entry of air. If the proximal end is clamped, the catheter cannot be reverse tunneled as described.

Therefore, there is a need for a catheter with integrated valve to provide protection at the proximal end of the catheter. In addition, for medical procedures requiring the implantation of a dual lumen catheter (e.g., hemodialysis catheter, etc.), it would be very difficult to tunnel the bifurcation connected to the proximal end of the catheter. Thus, it would be desirable to reverse tunnel the proximal portion of the dual lumen catheter prior to establishing a secure bifurcating connection with the dual lumen catheter.

It is also common to utilize a guidewire inserted in the vascular system to facilitate placement of a catheter, but its use can prevent capping the catheter to prevent fluid loss from or air entering the vascular system during placement. After catheter placement, it is common to attach a valved cap to the catheter connector(s) to prevent fluid loss from or air entering the catheter and vascular system. U.S. Pat. No. 6,575,960 (Bleed Back Control Assembly and Method) relates to a Y-valved connector. The 'Y-connector' includes a sealing valve that is normally closed except when accessed with a small diameter tube or wire. The sealing valve does not completely prevent air or fluid leakage, but relies on a second user compressible valve to provide a complete seal.

In short, there are several problems with the current valves. The flow path through the valve is restricted due to a restricted cross-sectional area, there is a dead space above or below the valve where blood accumulates, which makes it difficult to clean the valve, and the current valves are not designed for use with a guidewire traversing through the same valve. Also, the current valves cannot be accessed multiple times as they are typically screwed on to the catheter and discarded after use.

Therefore, there is a need for a valved catheter, which addresses shortcomings in the current products, reduces the risk of contamination, and permits repeated use thereof.

SUMMARY OF THE INVENTION

Accordingly, a valved catheter is described herein that includes an integral valve system intended to remain patent for the life of the catheter, which may be several years. During the life of the catheter, the valve should maintain functionality to provide multiple functions, including, but not limited to, one or more of the following examples: (a) sealing off the open end of the catheter during placement into the patient's circulation system, (b) sealing the catheter tube except when being accessed by an accessing device, such as a syringe or guidewire, to prevent blood loss or air embolism, (c) providing unobstructed flow to a fluid from an attachable unit, such as a bifurcation fitting, when attached to the catheter, (d) providing a safety valve with minimal dead space that automatically closes if the accessing device or attachable unit is disconnected from the catheter, to prevent blood loss or air embolism, and (e) providing for an "over the guidewire" placement or replacement technique. In one particular design, the valved catheter is configured to support at least the five functionalities listed above. In addition, it should be appreciated that other advantageous functions may also be provided by the valved catheter of the present invention.

In one variation a valved catheter comprises a catheter tube and a compression sleeve, said catheter tube including at least one lumen and having a necked portion formed in a proximal end thereof, said compression sleeve being positioned around said necked portion, wherein said at least one lumen is biased in a closed position at the necked portion by said compression sleeve, and wherein said at least one lumen assumes an open position when an attachable unit or accessing device is inserted through said necked portion.

In another variation, a bifurcating extension is provided for connection to the proximal end of the valved catheter. The bifurcating extension includes two stems at the distal end for engaging the valves in the catheter. In one particular design, each of the two stems comprises a rounded circumferential profile, which matches the corresponding lumen within the catheter. The bifurcating extension may include a locking interface for engaging and securing the bifurcating extension to the proximal end of the catheter.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

Figure 1:
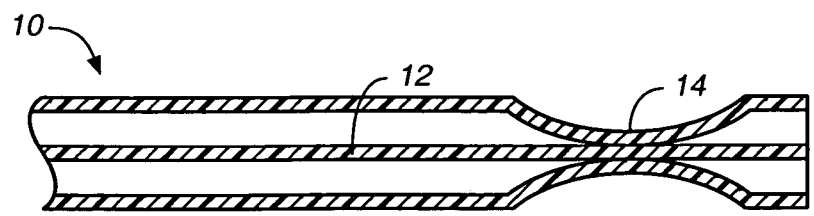
FIG. 1 is a cross-sectional view of one variation of a catheter tube implemented within the valved catheter.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other catheter implantation and connection devices for establishing a fluid conduit into a patient's body.

Reverse tunneling of an implanted dual lumen hemodialysis catheter with integrated valves is used herein as an example application of a valved catheter to illustrate the various aspects of the invention disclosed herein. In light of the disclosure herein, one of ordinary skill in the art would appreciate that variations of the valved catheter may be utilized with various connectors and instruments for establishing a fluid conduit into a patient's body. Although the valved catheter may be particularly useful in catheter implantation that requires reverse tunneling, it is contemplated that the valved catheter can also be utilized in various catheter implant procedures, which may not require reverse tunneling, to prevent embolism and/or facilitate establishment of a secured connection to the implanted catheter.

It must also be noted that, as used in this specification and the appended claims, the singular forms "a," "an" and "the" include plural referents unless the context clearly dictates otherwise. Thus, for example, the term "a valve" is intended to mean a single valve or a combination of valves, "a fluid" is intended to mean one or more fluids, or a mixture thereof. Furthermore, the words "proximal" and "distal" refer to directions closer to and away from, respectively, a physician operating the device, with the tip end (i.e., distal end) placed inside the patient's body. Thus, for example, the catheter end placed within the body of the patient would be the distal end of the catheter, while the catheter end outside the patient's body would be the proximal end of the catheter.

A valved catheter design that allows placement of attachable catheters (single or multiple lumen), while minimizing the risk of air embolism or blood loss through the open (proximal) end of the catheter tube, is disclosed herein. The valved design allows passage of a standard guidewire for 'over the guidewire' placement. The design prevents blood loss or air embolism from occurring if the catheter becomes detached from an attachable unit and when an accessing device is withdrawn therefrom. In one variation, the valved catheter includes a catheter tube having a necked portion in its proximal end that forms an integral valve, the necked portion being surrounded by a compression sleeve that biases the valve in a closed position. In a particular design configuration, the compression sleeve incorporates a compression wedge and a compression ring to improve valve closure. The valved catheter may be accessed by inserting a rigid stem(s) into the tube and through the valved area, permitting unimpeded flow through the catheter.

As stated, the valved catheter has an integral valve system. The catheter can be a single or multi-lumen configuration and can be made of any suitable material, such as silicone or polyurethane, for example. The valve seals the catheter tube except when being accessed by an accessing device, such as a syringe (for infusion or aspiration), or a guidewire, or an attachable unit, such as an attachable bifurcation. One of the purposes of the valve is to seal off the proximal end of the catheter during placement into the circulatory system. This prevents blood loss or air embolism that may occur if the catheter end is open, as in the case for a typical attachable catheters. With a syringe attached thereto, the catheter may be infused (flushed with saline) or aspirated to verify blood flow through the catheter. By utilizing the valved catheter according to the present invention, adapters and clamps become unnecessary.

In one variation, the valved catheter provides unobstructed flow of a fluid from an attachable unit, such as an attachable bifurcation, when attached to the catheter. Another design variation provides a safety valve with limited dead space that automatically closes if an accessing device or attachable unit is disconnected, in order to prevent blood loss or air embolism. In one particular design, the valved catheter has a dead space that is substantially zero. In another design variation the valved catheter provides for passage of a guidewire through the entire length of the catheter.

In yet another design variation, an adaptor is provided for coupling the proximal end of the valved catheter to a tunneler. For example, the adaptor may have a locking mechanism for engaging the proximal end of the valved catheter, and a proximal portion configured for receiving the barbed and/or tapered end of a tunneler. The adaptor may have a lumen, which extends from the distal end of the adaptor to the proximal end of the adaptor, configured to allow a guidewire to pass-through while the adaptor is connected to the proximal end of the valved catheter. The adaptor may also include a guidewire guide for centering the guidewire as the guidewire is inserted through the adaptor. In one variation, the proximal portion of the adaptor is configured to receive a syringe, such that the user can infuse and/or aspirate fluids in the catheter with the syringe. For example, the proximal lumen of the adaptor may be configured with a luer interface to engage a male luer on a syringe. Furthermore, a valve may be placed within the lumen of the adaptor to provide additional protection to the proximal opening of the catheter.

In one particular design, the valved catheter is configured such that a guidewire can be inserted into the catheter tip (i.e., the distal end) and passed through the length of the catheter and then through the integral valve at the proximal portion of the catheter. If an adaptor is attached to the proximal end of the catheter, the guidewire may enter the guidewire guide in the adaptor of the valved catheter before it passes through a valve and exits the adaptor assembly. Passing the guidewire through a valve may minimize risks associated with blood loss and/or air embolism. The valve may also prevent blood from spilling out of the proximal end of the catheter when the guidewire is pulled through the proximal end of the implanted valved catheter.

Figure 2:
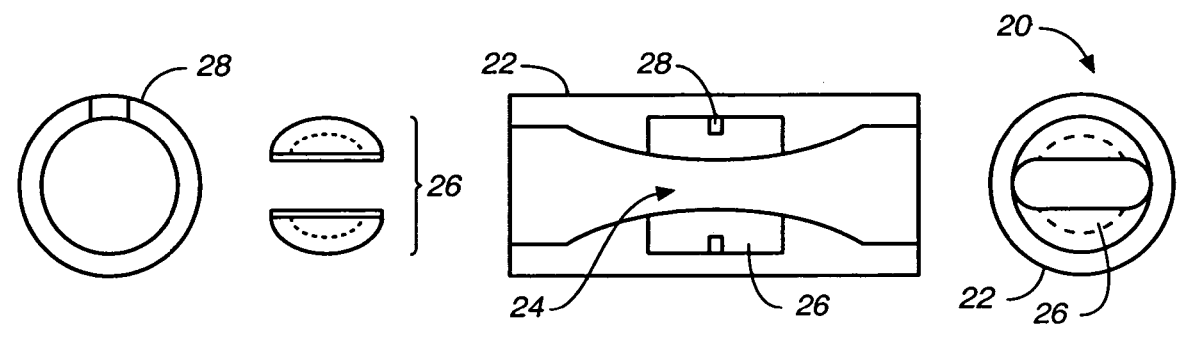
FIG. 2 are selected views of one variation of a compression sleeve and components thereof.
Figure 3:
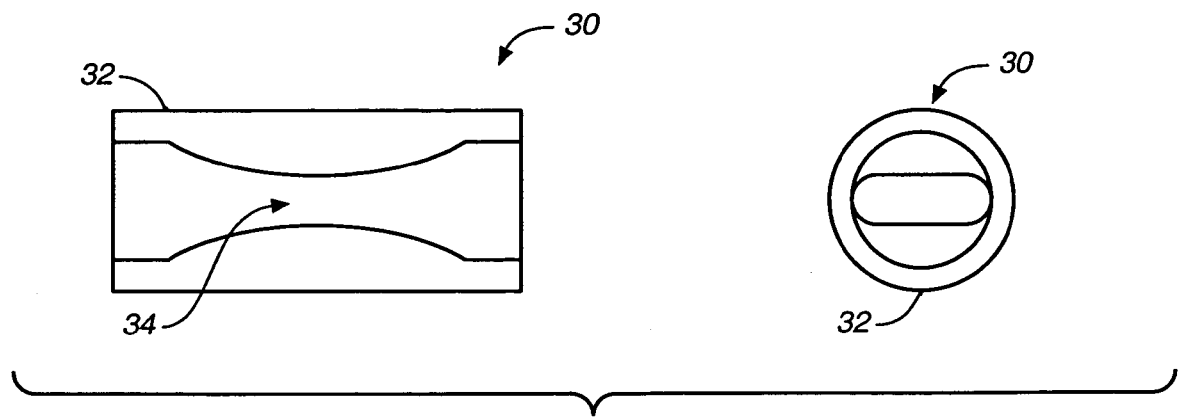
FIG. 3 includes a cross-sectional view and an end view of another variation of a compression sleeve.

FIGS. 1-3 illustrate separate components of one variation of a valved catheter. FIG. 1 shows a catheter tube 10 having a dual lumen configuration wherein separate lumens are divided by a septum 12. It should be noted that the present invention can equally be applied to a single lumen catheter or a catheter having more than two lumens. The catheter tube 10, preferably made of a pliable material, such as silicone or low durometer polyurethane, can be thermoformed or compression molded to form a necked portion 14 at the proximal end thereof. The necked portion 14 is formed, such that the outer wall of the catheter tube 10 on opposing sides thereof meet the septum 12, effectively closing the lumens to air and fluid. In one variation, a material that is relatively soft (e.g., with a hardness of approximately 40 (or lower) to 60 Shore A) is utilized to form the catheter tube 10 such that the force required to ensure closure thereof at the necked portion 14 is not so high that certain accessing devices would be precluded from use therewith.

FIG. 2 shows one variation of a compression sleeve for implementation over the catheter shown in FIG. 1. The compression sleeve is designed to be positioned around the necked portion 14 of the catheter tube 10 to ensure that the necked portion 14 closes for the life of the catheter tube 10 during implantation and when accessing devices or attachable units are withdrawn following insertion therethrough. The compression sleeve 20 includes a sleeve portion 22, which is formed to have a central passage for receiving the catheter tube 10, the central passage having a necked portion 24 fashioned to receive necked portion 14 of the catheter tube 10. Positioned around the necked portion 24 is a compression wedge 26 into which is formed a split compression ring 28. The split compression ring 28 may be composed of spring steel and may also be an overlapping ring design with split open ends to allow ring expansion when the valve is accessed and to facilitate valve closure when the accessing device is withdrawn. One of ordinary skill in the art having the benefit of this disclosure would recognize that there are many other mechanical spring assisted closing devices that could also be used. In addition, many different materials may be utilized to form the compression ring 28, including various metals and polymers. Together, the compression wedge 26 and the compression ring 28 provide the compression sleeve 20 with an inwardly directed force to ensure closure of the necked portion 14 of catheter tube 10 when the compression sleeve is placed therearound. It should be noted that in the compression sleeve 20 may be configured for permanent attachment to catheter tube 10.

FIG. 3 illustrates another variation of a compression sleeve. The compression sleeve 30 includes a sleeve portion 32, which is formed to have a central passage for receiving the catheter tube 10, the central passage having a necked portion 34 fashioned to receive the necked portion 14 of the catheter tube 10. In one variation, the compression sleeve 30 is made from a silicone material with resilient properties such that the necked portion 34 will assume its original shape following removal of a previously inserted accessing device or attachable unit from the necked portion 14 of the catheter tube 10. In one particular design, the compression sleeve 30 is made from a material having a hardness higher than that of the catheter tube 10. Thus, for example, a very soft catheter tube (e.g., approximately 40 Shore A or less) would be utilized with a compression sleeve having a hardness in the range of approximately 50 to 60 Shore A to provide the desired functionality, while a catheter tube having a hardness of about 60 Shore A or higher can be utilized with a compression sleeve having a hardness of approximately 70 Shore A or higher. These material configurations may also be applied a design with a compression sleeve that is only slightly larger than the catheter tube, to meet the goals of facilitated placement and patient comfort. Also contemplated are compression sleeves that have much larger diameters than the catheter tube, in which case, as the diameter of the compression sleeve increases, the desired hardness of the material generally decreases.

Figure 4:
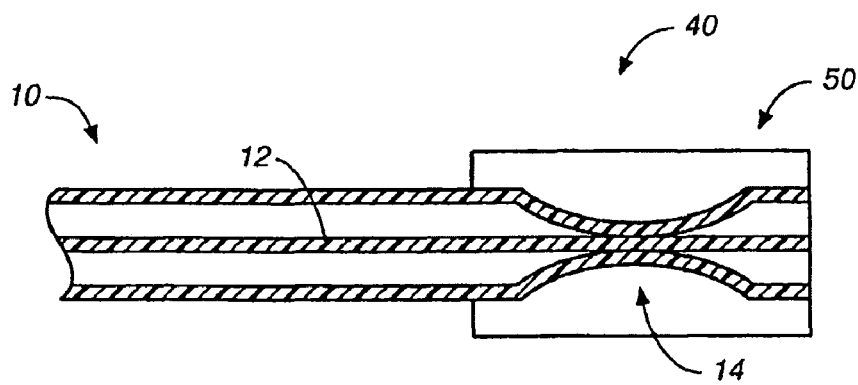
FIG. 4 is a cross-sectional view of a proximal end of one variation of a valved catheter.

FIG. 4 illustrates a valved catheter 40, wherein a compression sleeve 50 is permanently affixed to the proximal end of the catheter tube 10. Compression sleeve 50 may be formed according to compression sleeves 20 or 30, or the like, with the primary consideration being that compression sleeve 50 provides an inwardly directed force to the necked portion 14, such that in the absence of an accessing device or attachable unit inserted therethrough, the necked portion 14 remains tightly situated against septum 12. As mentioned above, such a configuration prohibits the passage of air or fluid through the necked portion 14, which is advantageous in placing catheter 10 into a body lumen, as well as providing protection at the proximal end of the catheter 10 after implantation, when it is desired to change or alternate accessing devices or attachable units. In the case of a single lumen design, the necked portion 14 may be tightly situated against itself (i.e., the opposing walls of the catheter would be in contact), and in the case of a design having more than two lumens, the necked portion can be tightly situated against perhaps more than one septum.

Figure 5:
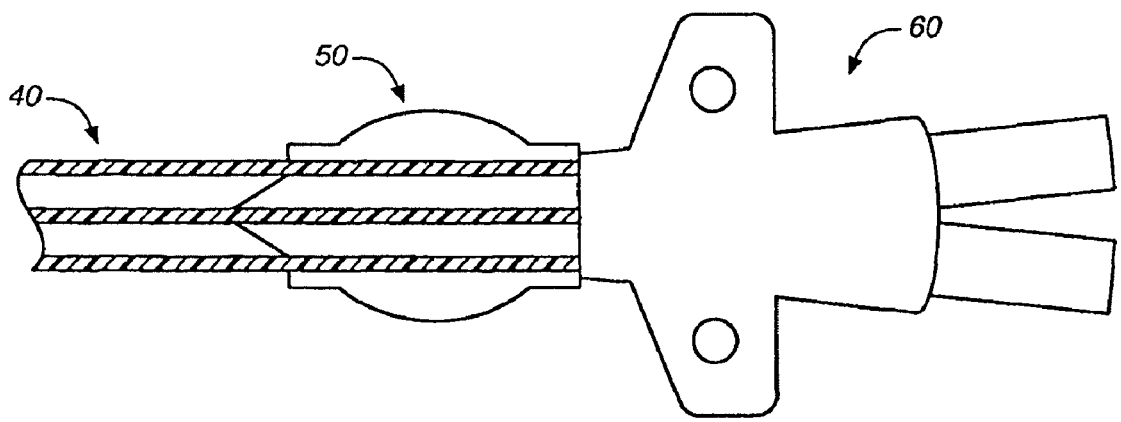
FIG. 5 is a cross-sectional view of an attachable bifurcation inserted into the proximal end of the valved catheter of FIG. 4.

FIG. 5 illustrates an attachable unit inserted into valved catheter 40. In this example, the attachable unit comprises an attachable bifurcation 60. When the attachable bifurcation 60, or any other attachable unit, is attached to the valved catheter 40, the flow of a fluid from the attachable bifurcation 60 into the catheter tube 10 is unobstructed by any restrictor such as a pinched or reduced opening. On the other hand, when the attachable bifurcation 60 is separated from the valved catheter 40, the valved catheter 40 automatically shuts off the flow of air or fluid therethrough due to the auto closure feature thereof, resulting from the pinching at the necked portion 14 of the catheter tube 10 by the compression sleeve 50. In one variation, the valve within the valved catheter 40 is configured such that without the attachable bifurcation 60 or other attachable unit or accessing device the valve would remain closed to prevent the flow of a fluid or air past the necked portion 14 under normal body pressure (both positive and negative), which, for example, may be approximately 1 psig (positive or negative) or less. In different variations, the valved catheter can be designed to allow the flow of a fluid past the necked portion at a fluid pressure of about ¼, ½, ¾ or 1 psig or higher (positive or negative).

In another variation, the valved catheter 40 is designed to have a high enough compression to seal above pressures (positive and negative) that are normally seen in the venous side of the circulatory system, but not so high of a compression such that it would be difficult or impossible to (a) pass a standard floppy tip guidewire therethrough, or (b) aspirate or infuse therethrough. In one design variation, the catheter tube 10 is made of a polyurethane material having a hardness in the range of approximately 70-75 Shore A, while the compression sleeve 50 is made of a silicone material having a hardness of approximately 80 Shore A. The valved catheter 40 may be designed to be small enough to fit within a cylindrical housing with dimensions of about 0.25 inch diameter or smaller and about 1.0 inch length or less to facilitate passage through a subcutaneous tunnel. A valved catheter with a relatively small proximal valved section can be attached to a tunneler, and then tunneled through a subcutaneous tunnel without causing much abrasion to the tissue wall within the subcutaneous channel.

In another variation, the attachable unit (e.g., an attachable bifurcation, etc.) may be configured with a locking mechanism for engaging the proximal end of the catheter. A connector hub may be provided at the proximal end of the valved catheter for interfacing the locking mechanism. An interface can also be integrated within the proximal end of the compression sleeve to receive the locking mechanism. The locking mechanism allows the user to secure the attachable unit to the catheter and prevent accidental detachment of the attachable unit. In one design, the user can simply apply a large enough force in the proximal direction to overcome the locking mechanism and to pull the attachable unit off the valved catheter. In another design, a latch may be provided such that the user needs to depressed the latch and disengaged the locking mechanism before the attachable unit can be removed. In yet another design, a tool is required to disengage the locking mechanism in order to remove the attachable unit.

In yet another variation, the valved catheter comprises a compression sleeve positioned over the valve portion of a catheter tube, and a connector hub is provided at the proximal end of the catheter tube for engaging and securing an attachable unit to the catheter tube. The compression sleeve and the connector hub may be glued, solvent bond, or otherwise secured onto the catheter. The catheter hub may comprise an interface for receiving a locking mechanism from the attachable unit, such that the attachable unit can engage the connector hub and be secured onto the proximal end of the valved catheter.

Figure 6:
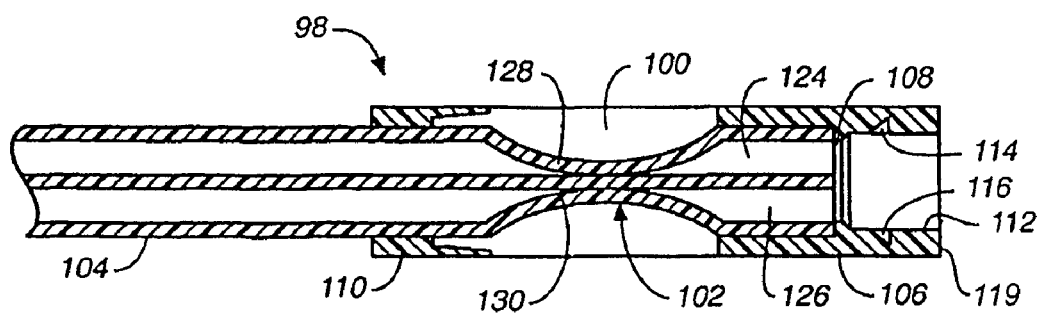
FIG. 6 is a cross-sectional view illustrating another variation of a valved catheter. In this variation, a locking interface is provided at the proximal end of the catheter to engage a bifurcating extension.

In one example, the valved catheter 98 comprises a compression sleeve 100 disposed over the neck portion 102 of the catheter tube 104, and a connector hub 106 is attached to the proximal end 108 of the catheter tube 104, as shown in FIG. 6. A retaining ring 110 is provided on the shaft of the catheter tube 104 and next to the distal end of the compression sleeve 100 to secure the compression sleeve 100 in place. The retaining ring 110 along with the connector hub 106 prevents the compression sleeve 100 from being displaced in either the proximal or the distal direction. In this particular example, the catheter tube 104 comprises a dual lumen polyurethane catheter; the compression sleeve 100 comprises silicone; the connector hub 106 comprises 65D polyurethane; and the retaining ring 110 comprises polyurethane. The undercut 112 at the proximal end of the connector hub 106 is configured with a pair of notches 114, 116 for engaging the locking mechanism on the attachable unit.

Figure 7A:
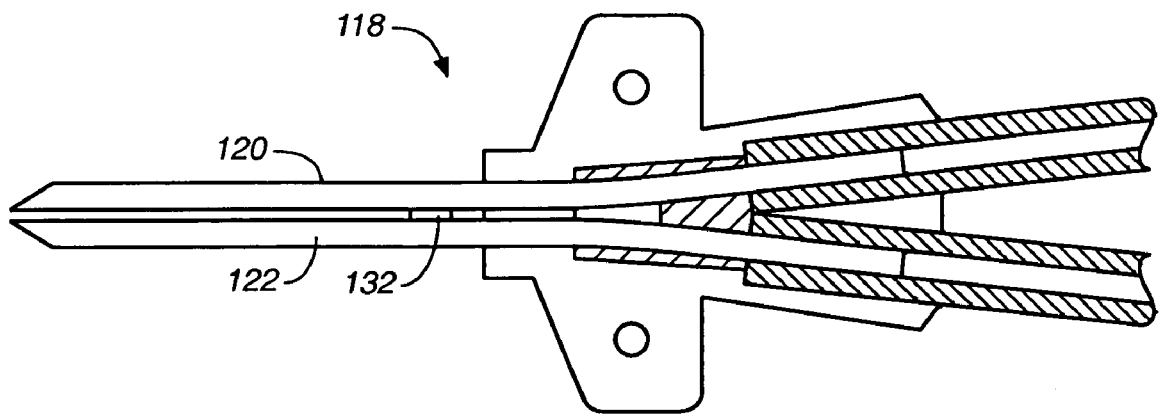
FIG. 7A is a top view showing the corresponding bifurcating extension for connection with the valved catheter of FIG. 6.
Figure 7B:
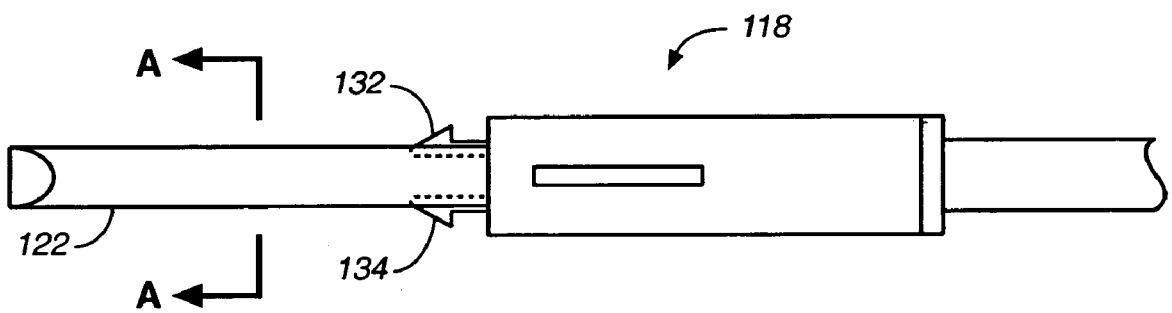
FIG. 7B is a side view of the bifurcating extension of FIG. 7A.
Figure 7C:
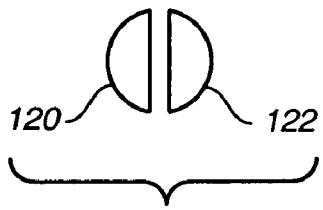
FIG. 7C is a cross-sectional view of the stems extending from the bifurcating extension of FIG. 7B. The cross-section is taken at A-A as shown in FIG. 7B.
Figure 7D:
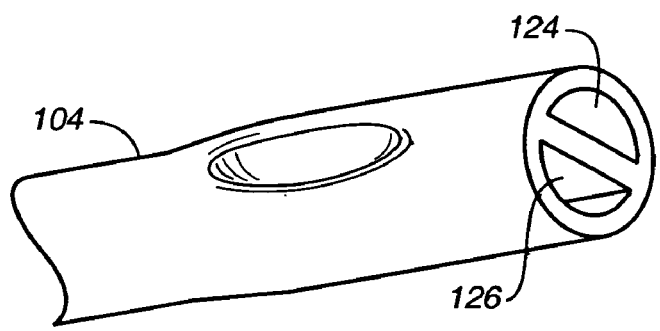
FIG. 7D illustrates one variation of a catheter tube configured for implementation with a compression sleeve. In this particular variation, the lumens of the catheter comprise "D"-shaped cross-sections.

FIG. 7A shows one possible configuration of an attachable unit 118 for insertion into the proximal end 120 of the valved catheter 98 shown in FIG. 6. In this particular example, the attachable unit 118 comprises an attachable bifurcate. The attachable bifurcate 118 includes two stems 120, 122 extending distally for insertion into the lumens 124, 126 of the catheter tube 104 to displace the valves 128, 130 and establish fluid communication channels. In addition, the attachable bifurcate 118 includes a pair of protruding clips 132, 134 (i.e., one variation of a locking mechanism) for engaging the notches 124, 126 within the under cut of the connector hub 106, as shown in FIG. 7B. Each of the stems 120, 122 includes at least a lumen for directing fluid flow in and out of the proximal end of the valved catheter 98. The stem may comprise various cross-sectional shapes. In one variation, each of the stems 120, 122 comprises a "D"-shaped cross-sectional profile, as shown in FIG. 7C. The corresponding valved catheter 98 may comprise a catheter tube 104 with matching "D"-shaped cross-sectional lumens 124, 126 for receiving the "D"-shaped stems 120, 122 on the attachable bifurcate 118, as shown in FIG. 7D.

Figure 8A:
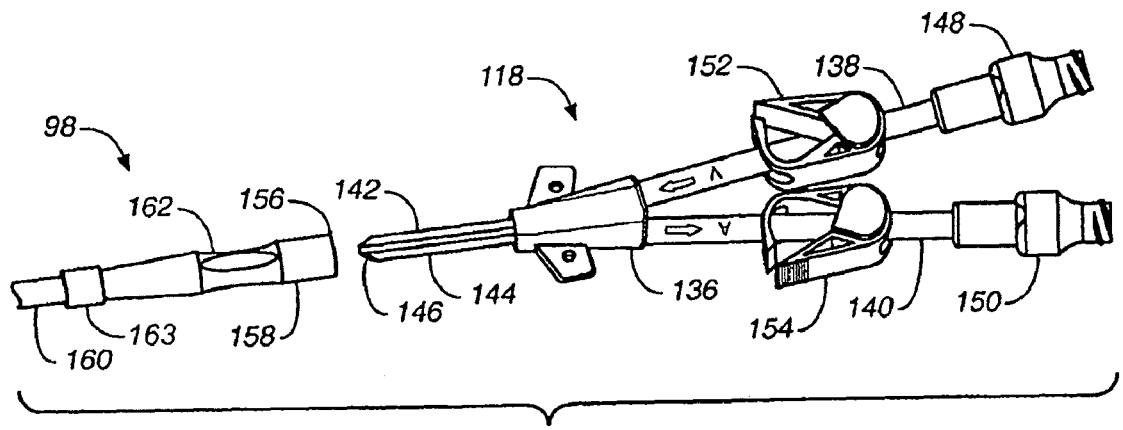
FIG. 8A illustrates one variation of a bifurcating extension configured for insertion into a corresponding dual lumen valved catheter.

In another example, the attachable unit 118 comprises a bifurcating extension configured for insertion into the proximal end of a valved catheter 98, as shown in FIG. 8A. In this example, the bifurcating extension 136 includes two extension tubings or legs 138, 140, each directing fluid flow from a corresponding stem 142, 144 (e.g., cannula, etc.) at the distal end 146 of the bifurcating extension 136. In one embodiment, each of the stems 142, 144 is about ⅝ of an inch long. Connector hubs 148, 150 are provided at the proximal end of the extension tubing 138, 140 to allow user to couple additional catheters or tubing to the valved catheter through the bifurcating extension 136. Optional clips 152, 154 may be provided on each of the extension tubings 138, 140 to control fluid flow through the extension tubing. The proximal end 156 of the valved catheter 98 comprises a connector hub 158 attached to the distal end of the catheter tubing 160. A silicone compression sleeve 162 is disposed over the neck portion of the catheter tubing 160, and a cuff 163 is provided to keep the silicone compression sleeve 162 in place.

Figure 8B:
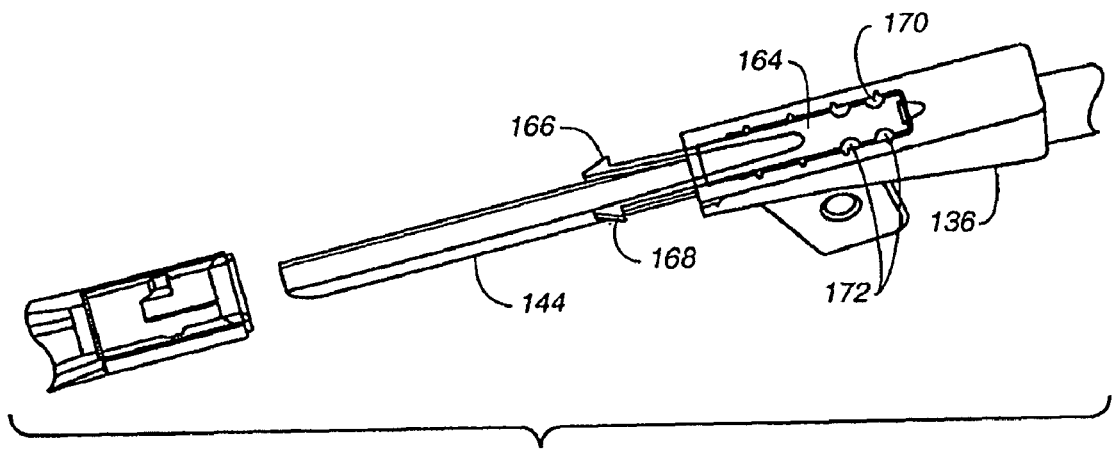
FIG. 8B is a cross-sectional view showing the connecting interface of the bifurcating extension of FIG. 8A.
Figure 8C:
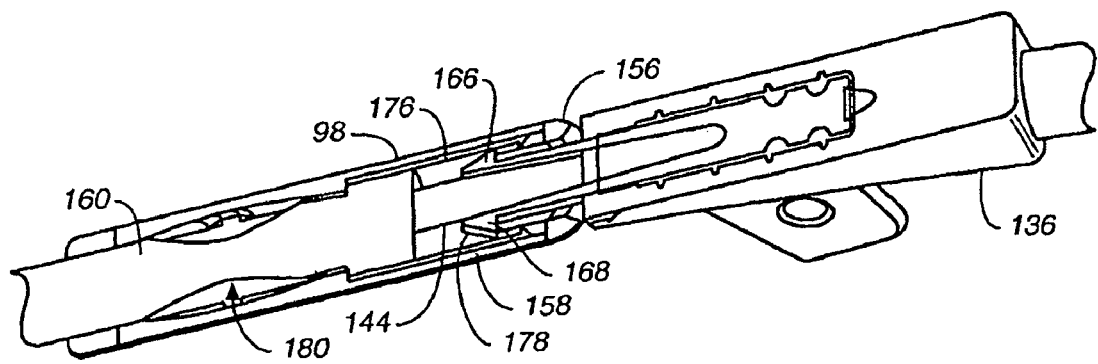
FIG. 8C is a cross-sectional view showing the bifurcating extension inserted within its corresponding valved catheter.

FIG. 8B is a cross-sectional view of the bifurcating extension 136 showing a metal latch 164 with a pair of protruding clips 166, 168 over-molded between the two stems 142, 144 and their corresponding extension tubing 138, 140. A hard plastic piece 170 with ridges 172 may be utilized to hold the metal latch 164 in place, before the over-mold is injected over the metal latch 164, the stems 142, 144, and the extension tubing 138, 140, to bond all the parts together. FIG. 8C shows a stem 144 from the bifurcating extension 136 inserted within the proximal end of the valved catheter. The clips 166, 168 engage the notches 176, 178 on the undercut of the hub connector 158, securing the bifurcating extension 136 onto the catheter 98. The stems 142, 144 are inserted through the neck portion 180 of the catheter tubing, forcing the valves in the catheter to be displaced.

Figure 9:
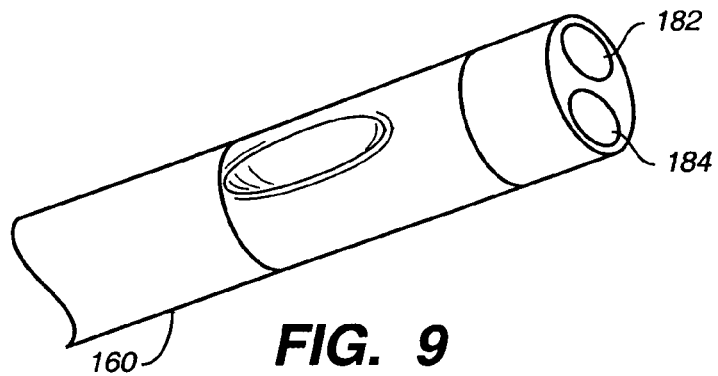
FIG. 9 illustrates another variation of a catheter tube configured for implementation with a compression sleeve. In this particular variation, the lumens of the catheter comprises rounded cross-sectional shapes.

In this example, each of the stems includes a rounded circumference matching the cross-section of the catheter tubing's lumen, which is also rounded. The rounded matching cross-sections may provide improved sealing when the stems are inserted into the proximal end of the catheter. The smooth/rounded transition between the inner lumen surface of the catheter and the outer circumferential surface of the stems results in improved contact, achieving a better seal therebetween. In particular, when a torque is exerted over the bifurcating extension in relation to the proximal portion of the catheter, the rounded interface between the lumen and the stem may be able to maintain a better seal in comparison to an interface with jagged corners. As shown in the example of FIG. 9, the catheter tubing 160 is configured with oval-shaped lumens 182, 184 for receiving stems 142, 144 with cross-sections that are oval or semi-oval. The stem and its corresponding lumens in the catheter may also be configured with other elliptical or circular shapes. One of ordinary skill in the art having the benefit of this disclosure would appreciate that the rounded matching interface for connecting an attachment unit to a receiving unit may be utilized with various fluid connectors that are well known to one of ordinary skill in the art.

Figure 10:
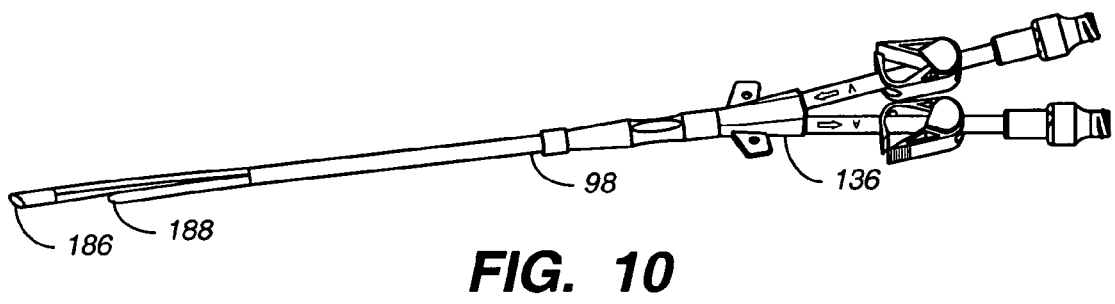
FIG. 10 illustrates the bifurcating extension of FIG. 8A inserted within its corresponding valved catheter. In this example, the distal end of the dual lumen catheter is configured with displaced distal lumen openings to serve as a hemodialysis catheter.

FIG. 10 is a perspective view showing the bifurcating extension 136 connected to the proximal end of the valved catheter 98. In this example, the valved catheter 98 is configured as a hemodialysis catheter. The distal end of the valved catheter 98 includes two displaced lumen openings 186, 188 that are typical on a catheter configured for hemodialysis application. To utilize this valved catheter 98, the user may insert a guidewire 190 into a patient's circulatory system and advance the guidewire until the tip of the guidewire is within the superior vena cava. An adaptor 192, such as the one shown in FIG. 11 may be attached onto the proximal end 156 of the valved catheter 98. The user then places the catheter's distal lumen opening 186 over the proximal end of the guidewire 190 and advances the valved catheter 98 towards the patient's heart (i.e., "over the guidewire" placement). The adaptor 192 may include a built-in valve 194 and a guidewire guide 196 for centering the guidewire 190. In this particular example, a polymeric structure 198 within the adaptor 192 is configured with hourglass-shaped lumen 200 for centering the guidewire 190 before the guidewire 190 is inserted into the slit valve 194 at the proximal end of the polymeric structure 196.

Figure 11:
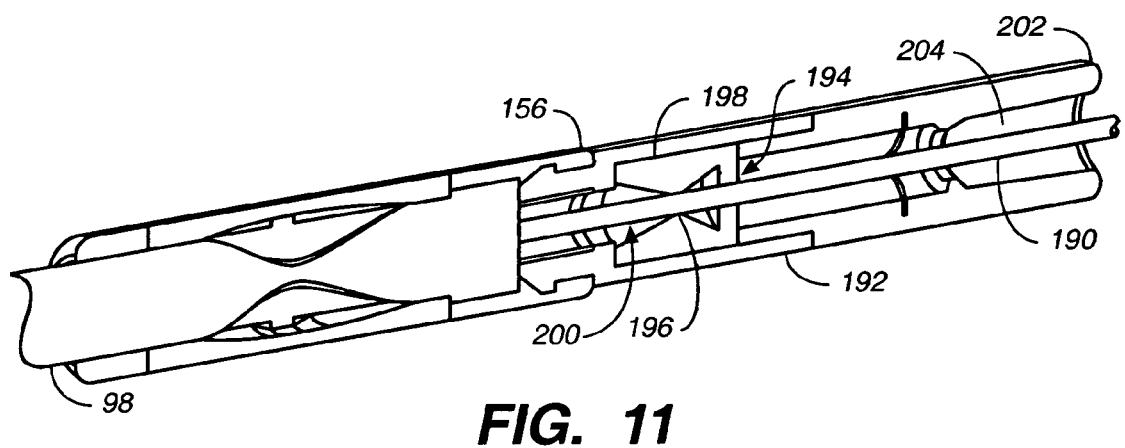
FIG. 11 illustrates a valved catheter with an adaptor coupled to the proximal end of the catheter, and a guidewire is inserted within one of the two lumens in the catheter tube.

Furthermore, the guidewire guide 196 may be configured to form as seal around the guidewire 190 as the guidewire is inserted therethrough. For example, as shown in FIG. 11, the inner diameter of the lumen at the neck portion of the guidewire guide 196 may be about the same as the outer diameter of the guidewire 190. The seal around the guidewire may prevent fluid from exiting the catheter and air from entering the catheter. In one variation, the adaptor 192 may be configured with only a guidewire guide 196 that is capable of forming a seal around the guidewire 190 and without the additional valve 194 positioned proximal of the guidewire guide 196.

As the user continues to advance the catheter 98, eventually the proximal end of the guidewire 190 passes through the valve 194 within the lumen of the adaptor 192, and exits at the proximal end 202 of the adaptor 192, as illustrated in FIG. 11. Once the catheter 98 is positioned in place, the user can pull out the guidewire 190 from the proximal end of the adaptor 192. The built-in valves prevents blood from spilling out of the proximal end of the device. The adaptor 192 may be further configured with a proximal lumen 204 that is configured to receive the male luer on a syringe, such that the user can remove trapped air in the implanted catheter by infusing or aspirating through the syringe. Once the adaptor 192 is removed, the user can insert a bifurcating extension 136 onto the proximal end 156 of the valved catheter 98. A dialysis machine may then be coupled to the implanted catheter through the bifurcating extension.

Figure 12:
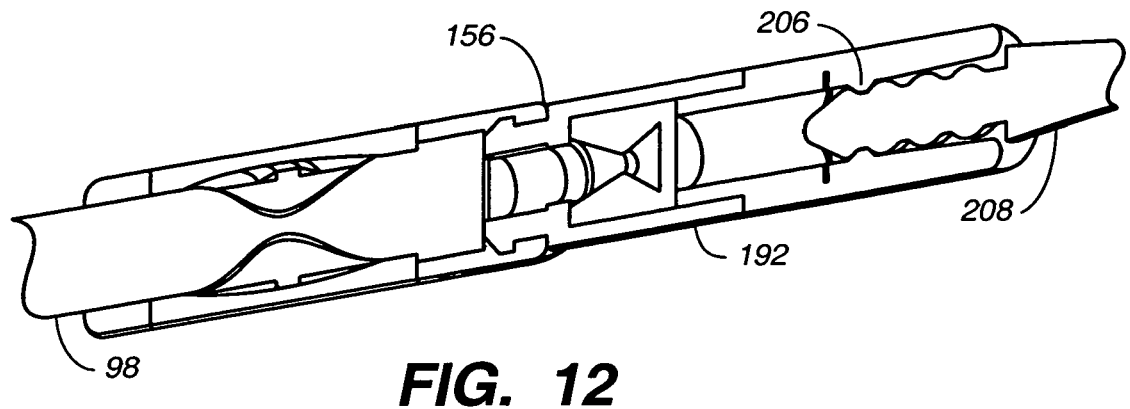
FIG. 12 illustrates adaptor/catheter unit of FIG. 11 with the guidewire removed and a tunneler coupled to the adaptor.

If reverse tunneling of the implanted catheter is desirable, the user may attach a tunneler onto the adaptor once the guidewire is removed. The user first inserts one end of the tunneler 208 through the tissue of the patient to form a subcutaneous channel. With the tunneler inserted through the subcutaneous channel, the user then attaches the proximal end of the adaptor to the tip of the tunneler that has passed through the subcutaneous channel. As shown in FIG. 12, the adaptor 192 is configured with an interface 206 for engaging and securing the tunneler 208. Once the catheter 98 is coupled to the tunneler 208 through the adaptor 192, the user can pull a proximal portion of the implanted catheter through the subcutaneous channel. With the proximal portion of the catheter 98 outside the exit site of the subcutaneous channel, the user can remove the tunneler 208 by disconnecting the adaptor 192 from the catheter 98. Once the adaptor 192 is removed, the user may then connect the bifurcating extension 136 onto the proximal end 156 of the valved catheter 98. With the bifurcating extension 136 connected, the user can then couple a dialysis machine to the implanted catheter 98.

It is also contemplated that the user may place the valved catheter into a patient's circulatory system without the assistance of an adaptor, through methods that are well known to one of ordinary skill in the art. Once the catheter is in place, if reverse tunneling is desirable, the user may then utilize an adaptor to connect the proximal end of the catheter to a tunneler. In another variation, a tunneler may be adapted with an interface to allow the user to directly couple the proximal end of the valved catheter to the tunneler.

Figure 13A:
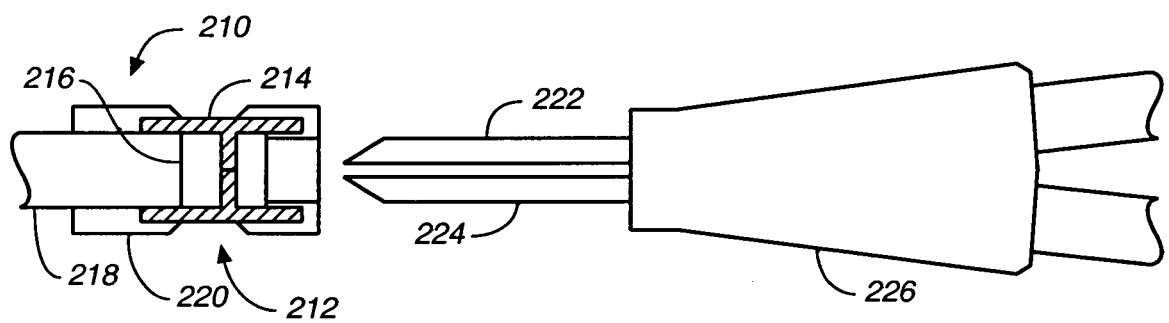
FIG. 13A illustrates another variation of a valved catheter and its corresponding bifurcating extension. In this variation the valve is provided within the connector hub attached to the proximal end of the catheter tube.
Figure 13B:
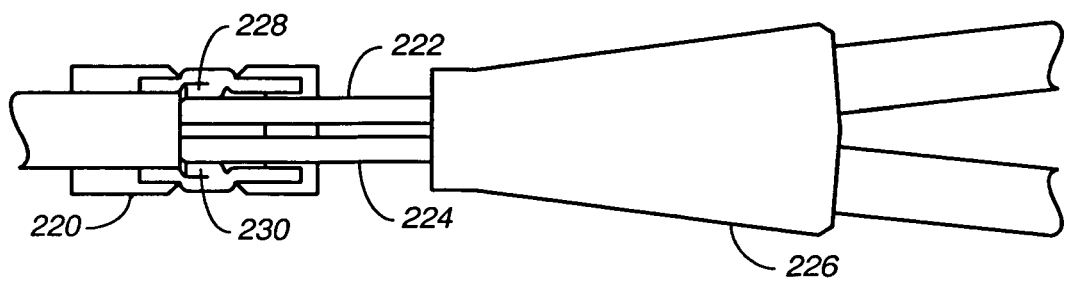
FIG. 13B illustrates the bifurcating extension of FIG. 13A inserted into the proximal end of the corresponding valved catheter.
Figure 14:
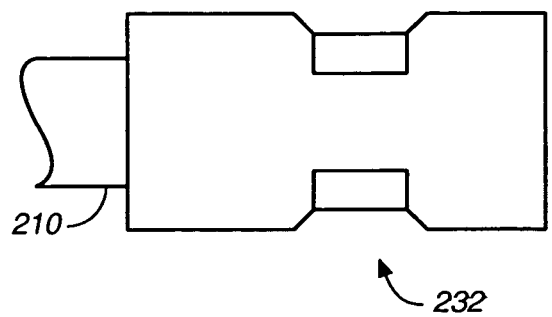
FIG. 14 a side view of the proximal portion of the valved catheter from FIG. 13A.
Figure 15A:
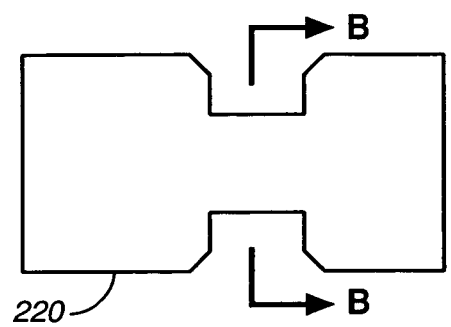
FIG. 15A is a side view of the valve housing from FIG. 14.
Figure 15B:
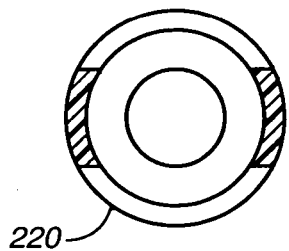
FIG. 15B is a cross-sectional view of the valve housing of FIG. 15A. The cross-section is taken at B-B as shown in FIG. 15A.
Figure 15C:
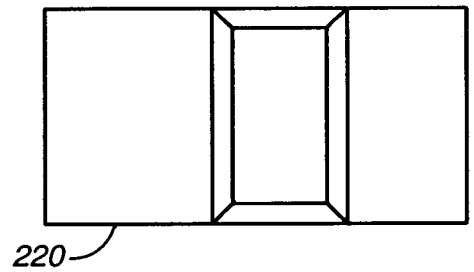
FIG. 15C is a top view of the valve housing of FIG. 15A.
Figure 16A:
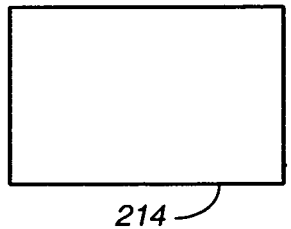
FIG. 16A is a side view of the valve from FIG. 13A.
Figure 16B:
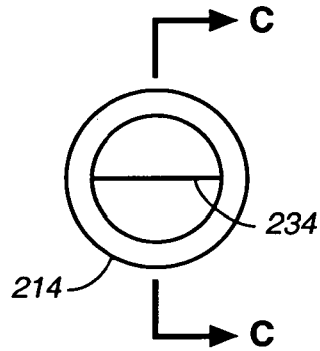
FIG. 16B is a frontal view of the valve of FIG. 16A.
Figure 16C:
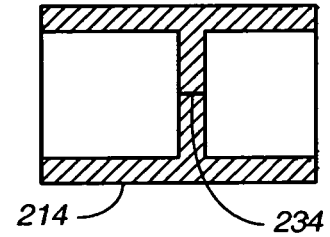
FIG. 16C is a cross-sectional view of the valve of FIG. 16B. The cross-section is taken at C-C as shown in FIG. 16B.

In another variation, the valved catheter 210 comprises a connector hub 212 with an integrated valve 214 attached to the proximal end 216 of a catheter tube 218. FIG. 13A shows one example where a connector hub housing 220 supports within its lumen a slit valve 214. The housing 220 may be comprised of polyurethane and the slit valve 214 may be comprised of silicone. FIG. 13A shows the valve 214 in the closed position. In FIG. 13B, the stems 222, 224 on the attachable bifurcate 226 are inserted through the connector hub housing 220 and into the proximal end 216 of the catheter tube 218. As the stems 222, 224 are forced through the connector hub housing 220, they displace the valve leaflets 228, 230 and allow fluid communication channels to be established through the two stems. FIG. 14 is a plan view illustrating the proximal portion 232 of the valved catheter 210. FIG. 15A is a side view of the connector hub housing 220. FIG. 15B shows the cross-sectional view of the connector hub housing 220. FIG. 15C is a top view of the connector hub housing 220. In FIG. 16A, the side view of the polymeric valve structure 214 is shown. FIG. 16B is a frontal view showing the slit opening 234 on the valve structure 214. FIG. 16C is a cross-sectional view of the valve structure 214.

Figure 17A:
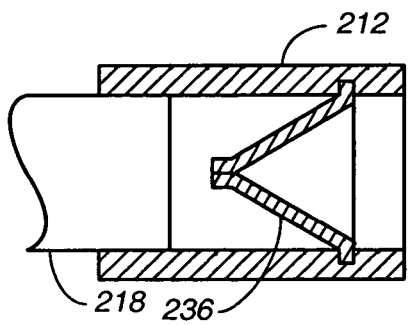
FIG. 17A is a cross-sectional view illustrating another variation of a valved catheter and its corresponding bifurcating extension. In this variation, a duckbill valve is provided within a connector hub, which is attached to the proximal end of the catheter tube.
Figure 17B:
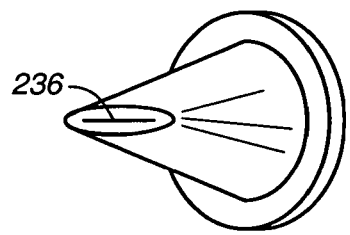
FIG. 17B is a perspective view of the duckbill valve from FIG. 17A.

In another variation, a duckbill valve 236 is implemented within the hub connector 212, which is coupled to the proximal end of a catheter tube 218, as shown in FIG. 17A. The valve 236 is shown in a non-engaged, closed position. FIG. 17B is a perspective view of the valve structure 236. One of ordinary skill in the art having the benefit of this disclosure would appreciate that the valve designs shown in FIG. 13A and FIG. 17A can easily be implanted on tubing with one, two, three or more lumens. Since the valve structure is not placed within the lumen of the catheter tube, a single design may be implanted over catheter tubes with varying number of lumens.

The proximal portion of the valved catheter may be designed for incorporation within a small housing that is compatible with multiple fittings (e.g., luer lock, slip fit, compression, etc). Valve function or performance is not affected by the addition of color or clear housing/components. Component or housing components are not affected by opacity or color. Markings and scales may be used on an as needed basis per application. Device function is not integrally linked to markings, etc. In one variation, the valved catheter comprises materials that are sterilizable using standard techniques (e.g., EtO, gamma, etc.). The methods of manufacturing the valved catheter of the different variations include machining or molding/forming the components of the catheter tube and compression sleeve.

Figure 18A:
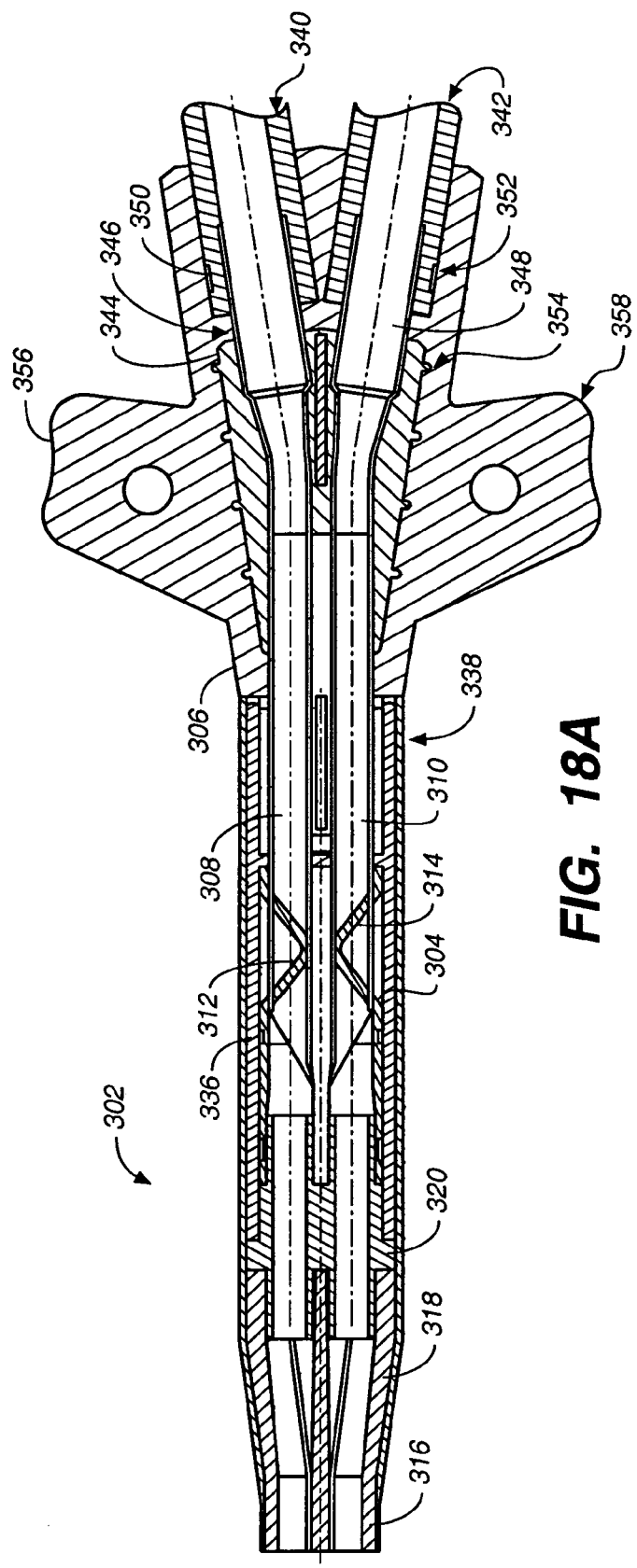
FIG. 18A illustrates another variation of a valved catheter. The valved catheter is shown with a bifurcation inserted into the proximal end of the catheter.

FIG. 18A illustrates another variation of a valved catheter 302. In this variation, a polymeric valve unit 304 is integrated into the proximal portion of the catheter 302. A bifurcation 306 is shown connected to the proximal end of the catheter 302 with the bifurcation's cannulas 308, 310 inserted into the distal portion of the valved catheter 302 to displace the valve mechanism 312, 314 and establish fluid communication. The valved catheter 302 comprises a catheter tubing 316 with a formed catheter shaft 318 at the proximal end of the tubing 316. In one variation, the catheter tubing 316 comprises polyurethane. A bridge 320 provides the interface between the polymeric valve unit 304 and the proximal end of the formed catheter shaft 318. In one variation, the bridge 320 comprises a material (e.g., a polymer, a combination of polymers, metal, metal alloyed, etc.) with a material hardness that is greater than the material hardness of the catheter tubing 316 and greater than the material hardness of the polymeric valve unit 304. The formed catheter shaft 318 is configured to receive the distal ends 322, 324 of the bridge 320. The proximal ends 326, 328 of the bridge 320 are configured for insertion into the two lumens 330, 332 at the distal end of the polymeric valve unit 304. The polymeric valve unit 304 comprises two lumens 330, 332 and a neck portion 334 that forms the valve mechanisms 312, 314 within the lumens 330, 332. In one variation, the polymeric valve unit comprises silicone. A valve housing 336 is positioned around the polymeric valve unit to secure the polymeric valve unit 304 in place. An oversleeve 338 is placed over the proximal portion of the catheter tubing 316, the bridge 320, and the valve housing 336. In one variation, the oversleeve 338 is heat formed over these components. In another variation, the oversleeve 338 is mechanically expanded and slipped over the components to hold them in place.

The bifurcation 306 comprises two extension tubings 340, 342 connected to the proximal end of the bifurcation overmold 344. The proximal ends 346, 348 of the cannulas 308, 310 interface with the extension tubings 340, 342. Each of the two extension tubings may be secured on its corresponding cannula by a ring clamp 350, 352. In one variation, the bifurcation 306 comprises a hard inner core sub-assembly 354 that is configured to secure the two cannulas 308, 310 in place. The overmold 344 of the bifurcation can be configured with two ears or flaps 356, 358. In one variation, the valved catheter and the corresponding bifurcation assembly is configured to support fluid communication of at least about 40 psi.

Figure 18B:
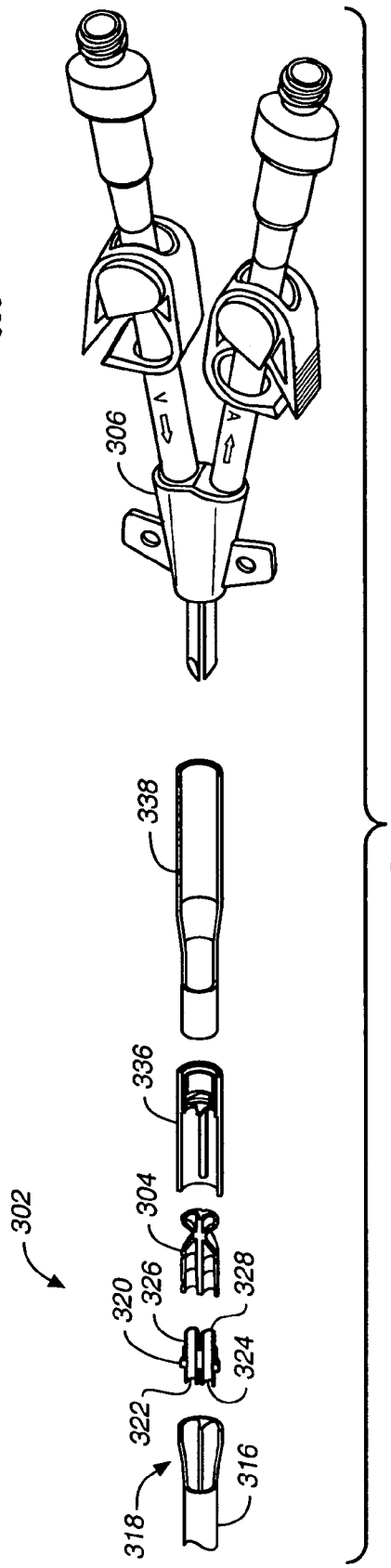
FIG. 18B shows the valved catheter of FIG. 18A with the bifurcation removed. The proximal portion of the valved catheter is shown in a disassembled state.
Figure 18C:
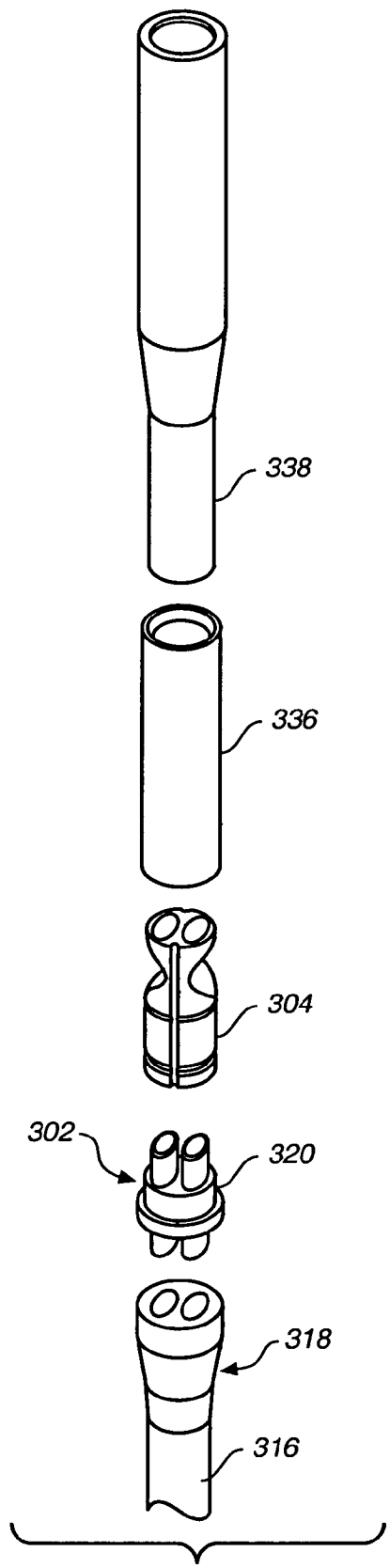
FIG. 18C is a perspective view, showing the various parts that form the proximal portion of the valved catheter of FIG. 18A.

In FIG. 18B, the bifurcation 306 is shown disconnected from the valved catheter 302, and the valved catheter 302 is shown in a disassembled condition. FIG. 18C is a perspective view showing the various parts of this particular variation of the valved catheter 302. As discussed above, the valved catheter 302 comprises a dual lumen catheter 316 with a formed catheter shaft 318, a bridge 320, a silicone valve 304, a valve housing 336, and an oversleeve 338.

Figure 18D:
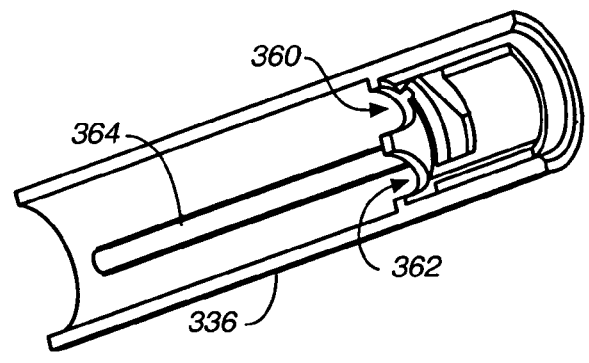
FIG. 18D is a cross-sectional view of the valve housing from FIG. 18C.
Figure 18E:
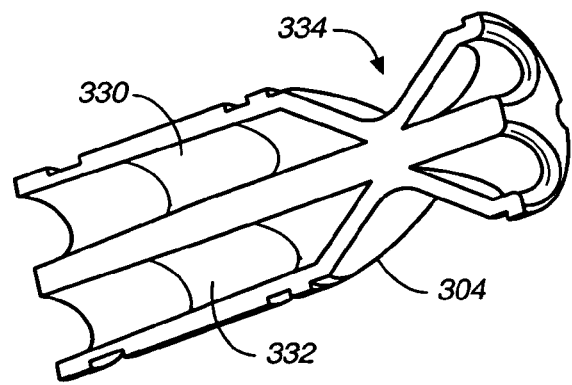
FIG. 18E is a cross-sectional view of the polymeric valve unit from FIG. 18C.
Figure 18F:
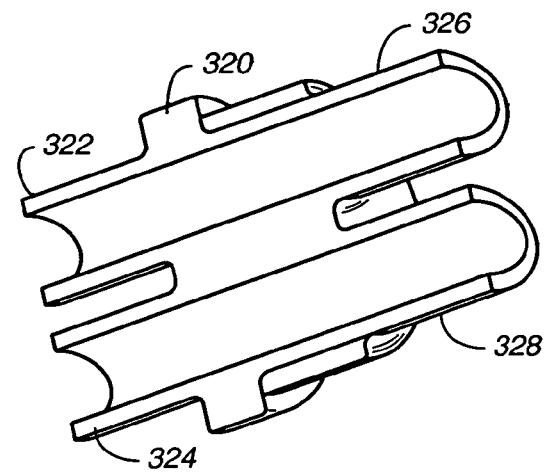
FIG. 18F is a cross-sectional view of the bridge from FIG. 18C.

FIG. 18D is a cross-sectional view of the valve housing 336. The inner lumen of the valve housing includes two orifices 360, 362 for receiving and/or guiding the two cannulas 308, 310 of the bifurcation 306 into the two corresponding lumens 330, 332 in the polymeric valve unit. One or more slots or raised profiles 364 are provided on the inner surface of the valve housing 336 to align the polymeric valve unit 304, such that the two lumens 330, 332 in the polymeric valve unit are aligned with the two orifices 360, 362. FIG. 18E is a cross-sectional view of the polymeric valve unit 304. In one variation, the polymeric valve unit 304 consists of silicone. The polymeric valve unit 304 comprises two lumens 330, 332 with a collapsed or necked section 334 which forms the valve mechanisms. When the cannulas 308, 310 from the bifurcation 306 are inserted within the lumens of the polymeric valve unit 304, the collapsed section 334 is displaced and fluid communication paths are established through the polymeric valve unit 304. Although in this example silicone is utilized to construct the polymeric valve unit 304, one of ordinary skill in the art would appreciate that other suitable polymeric materials may also be used. In another variation, the polymeric valve unit comprises a polymeric unit having two lumens. Each of the lumens includes a slit valve positioned within lumen, which seals the lumen when the polymeric valve unit is not engaged by the bifurcation's cannulas. FIG. 18F is a cross-sectional view of the bridge 320. The bridge is configured with two proximally extending legs 326, 328 for insertion into the two lumens 330, 332 at the distal end of the polymeric valve unit. The two distally extending legs 322, 324 of the bridge 320 are configured for insertion into the catheter lumens at the proximal end of the catheter tubing 316.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually set forth herein.

What is claimed as new and desired to be protected by Letters Patent of the United States is:

1. A valved catheter comprising:
   a catheter tube including two lumens, a proximal portion of each of the two lumens comprising a collapsed or necked lumen wall section forming a valve;
   an attachable bifurcate including two stems, each of the two stems being configured for insertion into one of the two lumens to displace the collapsed or necked wall section and establish fluid communication through the valve, the attachable bifurcate further including a locking mechanism for securing the attachable bifurcate to a proximal end of the catheter tube, the catheter tube further including a connector hub including a locking interface attached to the proximal end of the catheter tube, a compression sleeve disposed over the collapsed or necked lumen wall section, and a retaining ring positioned adjacent a distal end of the compression sleeve to prevent distal displacement thereof; and
   an adaptor including a distal end configured to engage the locking interface and a proximal portion configured to engage a tunneler.

2. The valved catheter according to claim 1, wherein each of the two lumens comprises a rounded cross-sectional shape.

3. The valved catheter according to claim 2, wherein each of the two stems comprises at least a partially rounded circumferential profile.

4. The valved catheter according to claim 2, wherein each of the two stems comprises a rounded circumferential profile which matches the rounded cross-sectional shape of the lumens.

5. The valved catheter according to claim 2, wherein the catheter tube further comprises a compression sleeve disposed over a proximal section of the catheter tube to compress the collapsed or necked lumen wall.

6. The valved catheter according to claim 5, wherein the catheter tube further comprises a connector hub attached to the proximal end of the catheter tube.

7. The valved catheter according to claim 6, wherein the catheter tube further comprises a retaining ring positioned adjacent a distal end of the compression sleeve to prevent distal displacement thereof.

* * * * *